US012252693B2

(12) United States Patent
Bordenstein et al.

(10) Patent No.: US 12,252,693 B2
(45) Date of Patent: Mar. 18, 2025

(54) **PLASMIDS FOR MANIPULATION OF *WOLBACHIA***

(71) Applicants: VANDERBILT UNIVERSITY, Nashville, TN (US); INSTITUT NATIONAL DE RECHERCHE POUR L'AGRICULTURE, L'ALIMENTATION ET L'ENVIRONNEMENT, Paris (FR); THE UNIVERSITY OF CHICAGO, Chicago, IL (US)

(72) Inventors: Sarah Bordenstein, Nashville, TN (US); Julie Reveillaud, Montpellier (FR); A. Murat Eren, Chicago, IL (US); Seth Bordenstein, Nashville, TN (US)

(73) Assignees: VANDERBILT UNIVERSITY, Nashville, TN (US); THE UNIVERSITY OF CHICAGO, Chicago, IL (US)

( * ) Notice: Subject to any disclaimer, the term of this patent is extended or adjusted under 35 U.S.C. 154(b) by 905 days.

(21) Appl. No.: 17/293,634

(22) PCT Filed: Nov. 15, 2019

(86) PCT No.: PCT/US2019/061611
§ 371 (c)(1),
(2) Date: May 13, 2021

(87) PCT Pub. No.: WO2020/102626
PCT Pub. Date: May 22, 2020

(65) Prior Publication Data

US 2022/0010317 A1 Jan. 13, 2022

Related U.S. Application Data

(60) Provisional application No. 62/768,165, filed on Nov. 16, 2018, provisional application No. 62/811,131, filed on Feb. 27, 2019.

(51) Int. Cl.
*C12N 15/74* (2006.01)

(52) U.S. Cl.
CPC ........ *C12N 15/74* (2013.01); *C12N 2800/101* (2013.01)

(58) Field of Classification Search
CPC .......................... C12N 15/74; C12N 2800/101
See application file for complete search history.

(56) References Cited

U.S. PATENT DOCUMENTS

2017/0112110 A1 4/2017 Hoang

FOREIGN PATENT DOCUMENTS

| | | |
|---|---|---|
| WO | 2017/181043 | 10/2017 |
| WO | 2017/214476 | 12/2017 |

OTHER PUBLICATIONS

Kent et al. Phage WO of Wolbachia: lambda of the endosymbiont world. Cell (2010), 18(4): 173-181. (Year: 2010).*

Baldridge et al. Transposon insertion reveals pRM, a plasmid of Rickettsia monacensis. Appl and Environ Microbiol (2007), 73(15):4984-4995. (Year: 2007).*

International Search Report and Written Opinion dated Feb. 20, 2020, from International Application No. PCT/US2019/061611, 11 pages.

Reveillaud, et al. "The Wolbachia mobilome in Culex pipiens includes a putative plasmid", Nate Communications, (2019)10:1051.

El Karkouri et al. "Origin and Evolution of Rickettsial Plasmids", PLOS ONE, Feb. 16, 2016.

Gillespie et al. "A Tangled Web: Origins of Reproductive Parasitism", Genome Biol. Evol. 10(9):2292-2309.

Oki et al. "Dendrimer-enabled transformation of Anaplasma phagocytophilum", Microbes and Infection 17 (2015) 817-822.

Alberti, Adriana et al. 2017. "Viral to Metazoan Marine Plankton Nucleotide Sequences from the Tara Oceans Expedition." *Scientific Data* 4:1-20.

Alneberg, Johannes et al. 2014. "Binning Metagenomic Contigs by Coverage and Composition." *Nature Methods* 11:1144. Retrieved (http://dx.doi.org/10.1038/nmeth.3103).

Altschul, Stephen F., et al. "Basic local alignment search tool." Journal of molecular biology 215.3 (1990): 403-410.

Altschul, Stephen F., et al. "Gapped BLAST and PSI-BLAST: a new generation of protein database search programs." Nucleic acids research 25.17 (1997): 3389-3402.

Andrews, Elizabeth S., Philip R. Crain, Yuqing Fu, Daniel K. Howe, and Stephen L. Dobson. 2012. "Reactive Oxygen Species Production and Brugia Pahangi Survivorship in Aedes Polynesiensis with Artificial Wolbachia Infection Types." *PLoS Pathogens* 8(12).

(Continued)

*Primary Examiner* — Iqbal H Chowdhury

(74) *Attorney, Agent, or Firm* — Meunier Carlin & Curfman LLC

(57) ABSTRACT

The present disclosure relates to plasmids, systems, and methods for the transformation of *Wolbachia*. Disclosed herein are plasmids and systems for use in methods of transforming *Wolbachia*. The inventors have identified extrachromosomal plasmids within *Wolbachia*. Disclosed herein is a non-naturally occurring plasmid comprising a nucleic acid encoding a transposase. Disclosed herein is a method for transforming a *Wolbachia* cell, comprising introducing a non-naturally occurring plasmid into the cell, wherein the plasmid comprises a nucleic acid sequence capable of transforming a *Wolbachia* cell.

18 Claims, 7 Drawing Sheets

Specification includes a Sequence Listing.

(56) References Cited

OTHER PUBLICATIONS

Ant, Thomas H., Christie S. Herd, Vincent Geoghegan, Ary A. Hoffmann, and Steven P. Sinkins. 2018. "The Wolbachia Strain WAu Provides Highly Efficient Virus Transmission Blocking in Aedes Aegypti." *PLoS Pathogens* 14(1):1-19.
Atyame, Célestine M et al. 2014. "Wolbachia Divergence and the Evolution of Cytoplasmic Incompatibility in Culex Pipiens." *PLoS ONE* 9(1):21-26.
Baldridge, Gerald D., Nicole Y. Burkhardt, Roderick F. Felsheim, Timothy J. Kurtti, and Ulrike G. Munderloh. 2007. "Transposon Insertion Reveals PRM, a Plasmid of Rickettsia Monacensis." *Applied and Environmental Microbiology* 73(15):4984-95.
Beaucage, S. L., and M. H. Caruthers. "Deoxynucleoside phosphoramidites—a new class of key intermediates for deoxypolynucleotide synthesis." Tetrahedron letters 22.20 (1981): 1859-1862.
Beckmann, John F., Judith A. Ronau, and Mark Hochstrasser. 2017. "A Wolbachia Deubiquitylating Enzyme Induces Cytoplasmic Incompatibility." *Nature Microbiology* 2:17007. Retrieved (http://dx.doi.org/10.1038/nmicrobiol.2017.7).
Bian, Guowu et al. 2013. "Wolbachia Invades Anopheles Stephensi Populations and Induces Refractoriness to Plasmodium Infection." *Science* 340(6133).
Blagrove, M. S. C., C. Arias-Goeta, A. B. Failloux, and S. P. Sinkins. 2012. "Wolbachia Strain WMel Induces Cytoplasmic Incompatibility and Blocks Dengue Transmission in Aedes Albopictus." *Proceedings of the National Academy of Sciences* 109(1):255-60. Retrieved (http://www.pnas.org/cgi/doi/10.1073/pnas.1112021108).
Bonneau, Manon et al. 2018. "Culex Pipiens Crossing Type Diversity Is Governed by an Amplified and Polymorphic Operon of Wolbachia." *Nature Communications* 9(1):319. Retrieved (https://doi.org/10.1038/s41467-017-02749-w).
Bordenstein, S. R. and J. H. Werren. 2007. "Bidirectional Incompatibility among Divergent Wolbachia and Incompatibility Level Differences among Closely Related Wolbachia in Nasonia." *Heredity* 99(3):278-87.
Bordenstein, Sarah R. and Seth R. Bordenstein. 2016. "Eukaryotic Association Module in Phage WO Genomes from Wolbachia." *Nature Communications* 7:1-10. Retrieved (http://dx.doi.org/10.1038/ncomms13155).
Bordenstein, Seth R. and Jennifer J. Wernegreen. 2004. "Bacteriophage Flux in Endosymbionts (Wolbachia): Infection Frequency, Lateral Transfer, and Recombination Rates." *Molecular Biology and Evolution* 21(10):1981-91.
Boyer, Sébastien, Elodie Calvez, Thais Chouin-Carneiro, Diawo Diallo, and Anna Bella Failloux. 2018. "An Overview of Mosquito Vectors of Zika Virus." *Microbes and Infection*.
Burkhardt, Nicole Y. et al. 2011. "Development of Shuttle Vectors for Transformation of Diverse Rickettsia Species." *PLoS ONE* 6(12).
Campbell, J. H. et al. 2013. "UGA Is an Additional Glycine Codon in Uncultured SR1 Bacteria from the Human Microbiota." *Proceedings of the National Academy of Sciences* 110(14):5540-45. Retrieved (http://www.pnas.org/cgi/doi/10.1073/pnas.1303090110).
Cerveau, Nicolas, Sébastien Leclercq, Elodie Leroy, Didier Bouchon, and Richard Cordaux. 2011. "Short- and Long-Term Evolutionary Dynamics of Bacterial Insertion Sequences: Insights from Wolbachia Endosymbionts." *Genome Biology and Evolution* 3(1):1175-86.
Cerveny, Lukas et al. 2013. "Tetratricopeptide Repeat Motifs in the World of Bacterial Pathogens: Role in Virulence Mechanisms." *Infection and Immunity* 81(3):629-35.
Chafee, Meghan E., Daniel J. Funk, Richard G. Harrison, and Seth R. Bordenstein. 2010. "Lateral Phage Transfer in Obligate Intracellular Bacteria (Wolbachia): Verification from Natural Populations." *Molecular Biology and Evolution* 27(3):501-5.
Conner, William R. et al. 2017. "Genome Comparisons Indicate Recent Transfer of WRi-like Wolbachia between Sister Species *Drosophila suzukii* and *D. subpulchrella." Ecology and Evolution* 7(22):9391-9404.
Coren, Jonathon S., James C. Pierce, and Nat Sternberg. 1995. "Headful Packaging Revisited: The Packaging of More than One DNA Molecule into a Bacteriophage P1 Head." *Journal of Molecular Biology* 249(1):176-84.
Delmont, Tom O. and A. Murat Eren. 2016. "Identifying Contamination with Advanced Visualization and Analysis Practices: Metagenomic Approaches for Eukaryotic Genome Assemblies." *PeerJ* 4:e1839. Retrieved (https://peerj.com/articles/1839).
Delmont, Tom O. and A. Murat Eren. 2018. "Linking Pangenomes and Metagenomes: The *Prochlorococcus* Metapangenome." *PeerJ* 6:e4320. Retrieved (https://peerj.com/articles/4320).
El Karkouri, Khalid, Pierre Pontarotti, Didier Raoult, and Pierre Edouard Fournier. 2016. "Origin and Evolution of Rickettsial Plasmids." *PLoS ONE* 11(2):1-17.
Eren, A. Murat et al. 2015. "Anvi'o: An Advanced Analysis and Visualization Platform for 'omics Data." *PeerJ* 3:e1319. Retrieved (https://peerj.com/articles/1319).
Eren, A. Murat, Joseph H. Vineis, Hilary G. Morrison, and Mitchell L. Sogin. 2013. "A Filtering Method to Generate High Quality Short Reads Using Illumina Paired-End Technology." *PLoS ONE* 8(6):6-11.
Ferree, Patrick M. et al. 2005. "Wolbachia Utilizes Host Microtubules and Dynein for Anterior Localization in the *Drosophila oocyte*." *PLoS Pathogens* 1(2):0111-24.
Flores, Heather A. and Scott L. O'Neill. 2018. "Controlling Vector-Borne Diseases by Releasing Modified Mosquitoes." *Nature Reviews Microbiology* 1.
Folmer, Ole, Michael Black, Hoeh Wr, R. Lutz, and Robert Vrijenhoek. 1994. *DNA Primers for Amplification of Mitochondrial Cytochrome C Oxidase Subunit I from Diverse Metazoan Invertebrates*.
Funkhouser-Jones, Lisa J., Edward J. van Opstal, Ananya Sharma, and Seth R. Bordenstein. 2018. "The Maternal Effect Gene Wds Controls Wolbachia Titer in Nasonia." *Current Biology* 28(11):1692-1702.e6. Retrieved (https://doi.org/10.1016/j.cub.2018.04.010).
Gamston, Courtney, and Jason Rasgon. "Maintaining Wolbachia in cell-free medium." JoVE (Journal of Visualized Experiments) 5 (2007): e223. Abstract.
Gould, Ernest, John Pettersson, Stephen Higgs, Remi Charrel, and Xavier de Lamballerie. 2017. "Emerging Arboviruses: Why Today?" *One Health* 4(April):1-13.
Harms, Alexander, Ditlev Egeskov Brodersen, Namiko Mitarai, and Kenn Gerdes. 2018. "Toxins, Targets, and Triggers: An Overview of Toxin-Antitoxin Biology." *Molecular Cell* 1-17. Retrieved (https://doi.org/10.1016/j.molcel.2018.01.003).
Hedges, Lauren M., Jeremy C. Brownlie, Scott L. O'Neill, and Karyn N. Johnson. 2008. "Wolbachia and Virus Protection in Insects." *Science* 322(5902):702.
Henikoff, Steven, and Jorja G. Henikoff. "Amino acid substitution matrices from protein blocks." Proceedings of the National Academy of Sciences 89.22 (1992): 10915-10919.
Hyatt, Doug et al. 2010. "Prodigal: Prokaryotic Gene Recognition and Translation Initiation Site Identification." *BMC Bioinformatics* 11.
Ishmael, Nadeeza et al. 2009. "Extensive Genomic Diversity of Closely Related Wolbachia Strains." *Microbiology* 155(7):2211-22.
Iturbe-Ormaetxe, Iñaki, Megan Woolfit, Edwige Rancès, Anne Duplouy, and Scott L. ONeill. 2011. "A Simple Protocol to Obtain Highly Pure Wolbachia Endosymbiont DNA for Genome Sequencing." *Journal of Microbiological Methods* 84(1):134-36.
Jeffries, Claire L. and Thomas Walker. 2016. "Wolbachia Biocontrol Strategies for Arboviral Diseases and the Potential Influence of Resident Wolbachia Strains in Mosquitoes." *Current Tropical Medicine Reports* 3(1):20-25. Retrieved (http://link.springer.com/10.1007/s40475-016-0066-2).
Joubert, D. Albert et al. 2016. "Establishment of a Wolbachia Superinfection in Aedes Aegypti Mosquitoes as a Potential Approach for Future Resistance Management." *PLoS Pathogens* 12(2):1-19.
Joubert, Dirk Albert and Scott L. O'Neill. 2017. "Comparison of Stable and Transient Wolbachia Infection Models in Aedes Aegypti to Block Dengue and West Nile Viruses." *PLoS Neglected Tropical Diseases* 11(1):1-14.

(56) References Cited

OTHER PUBLICATIONS

Karlin, Samuel, and Stephen F. Altschul. "Applications and statistics for multiple high-scoring segments in molecular sequences." Proceedings of the National Academy of Sciences 90.12 (1993): 5873-5877.

Kent, Bethany N., Leonidas Salichos, et al. 2011. "Complete Bacteriophage Transfer in a Bacterial Endosymbiont (Wolbachia) Determined by Targeted Genome Capture." Genome Biology and Evolution 3(1):209-18.

Kent, Bethany N., Lisa J. Funkhouser, Shefali Setia, and Seth R. Bordenstein. 2011. "Evolutionary Genomics of a Temperate Bacteriophage in an Obligate Intracellular Bacteria (Wolbachia)." *PLoS ON3E* 6(9).

Klasson, L. et al. 2009. "The Mosaic Genome Structure of the Wolbachia WRi Strain Infecting Drosophila Simulans." *Proceedings of the National Academy of Sciences* 106(14):5725-30. Retrieved (http://www.pnas.org/cgi/doi/10.1073/pnas.0810753106).

Klasson, Lisa et al. 2008. "Genome Evolution of Wolbachia Strain WPip from the Culex Pipiens Group." *Molecular Biology and Evolution* 25(9):1877-87.

Konieczny, Igor, Katarzyna Bury, Aleksandra Wawrzycka, and Katarzyna Wegrzyn. 2014. "Iteron Plasmids." *Microbiology Spectrum* 2(6):1-16. Retrieved (http://www.asmscience.org/content/journal/microbiolspec/10.1128/microbiolspec.PLAS-0026-2014).

Köster, Johannes and Sven Rahmann. 2012. "Snakemake—a Scalable Bioinformatics Workflow Engine." *Bioinformatics* 28(19):2520-22. Retrieved (http://dx.doi.org/10.1093/bioinformatics/bts480).

Langmead, Ben and Steven L. Salzberg. 2012. "Fast Gapped-Read Alignment with Bowtie 2." *Nature Methods* 9:357. Retrieved (http://dx.doi.org/10.1038/nmeth.1923).

Laven, H. 1967. "A Possible Model for Speciation by Cytoplasmic Isolation in the Culex Pipiens Complex." *Bulletin of the World Health Organization* 37(2):263-66.

Leffers, Gerald and Venigalla Basaveswara Rao. 1996. "A Discontinuous Headful Packaging Model for Packaging Less Than Headful Length DNA Molecules by Bacteriophage T4." *Journal of Molecular Biology* 258(5):839-50. Retrieved (http://www.sciencedirect.com/science/article/pii/S0022283696902910).

LePage, Daniel and Seth R. Bordenstein. 2013. "Wolbachia: Can we Save Lives with a Great Pandemic?" *Trends in Parasitology* 29(8):385-93.

LePage, Daniel P. et al. 2017. "Prophage WO Genes Recapitulate and Enhance Wolbachia-Induced Cytoplasmic Incompatibility." *Nature* 543:243. Retrieved (http://dx.doi.org/10.1038/nature21391).

Letunic, Ivica and Peer Bork. 2018. "20 Years of the SMART Protein Domain Annotation Resource." *Nucleic Acids Research* 46(D1):D493-96. Retrieved (http://dx.doi.org/10.1093/nar/gkx922).

Lo, Nathan, Maurizio Casiraghi, Emanuela Salati, Chiara Bazzocchi, and Claudio Bandi. 2002. "How Many Wolbachia Supergroups Exist?" *Molecular Biology and Evolution* 19(3):341-46. Retrieved (http://dx.doi.org/10.1093/oxfordjournals.molbev.a004087).

Marchler-Bauer, Aron et al. 2002. "Cdd: A Database of Conserved Domain Alignments with Links to Domain Three-Dimensional Structure." *Nucleic Acids Research* 30(1):281-83.

Matteucci, Mark Douglas, and M. Ho Caruthers. "Synthesis of deoxyoligonucleotides on a polymer support." Journal of the American Chemical Society 103.11 (1981): 3185-3191.

McMeniman, Conor J. et al. 2009. "Stable Introduction of a Life-Shortening <Em>Wolbachia</Em> Infection into the Mosquito <Em>Aedes Aegypti</Em>" *Science* 323(5910):141 LP-144. Retrieved (http://science.sciencemag.org/content/323/5910/141.abstract).

Ogata, Hiroyuki et al. 2005. "The Genome Sequence of Rickettsia Felis Identifies the First Putative Conjugative Plasmid in an Obligate Intracellular Parasite." *PLoS Biology* 3(8).

Pan, Xiaoxiao, Anja Lührmann, Ayano Satoh, Michelle A. Laskowski-Arce, and Craig R. Roy. 2008. "Ankyrin Repeat Proteins Comprise a Diverse Family of Bacterial Type IV Effectors." *Science* (*New York, N.Y.*) 320(5883):1651-54. Retrieved (http://www.ncbi.nlm.nih.gov/pmc/articles/PMC2514061/).

Peng, Yu, Henry C. M. Leung, S. M. Yiu, and Francis Y. L. Chin. 2012. "IDBA-UD: A de Novo Assembler for Single-Cell and Metagenomic Sequencing Data with Highly Uneven Depth." *Bioinformatics* 28(11):1420-28.

Petridis, Michael and Dimitrios Chatzidimitriou. 2011. "Characterization of an Intergenic Polymorphic Site (Pp-HC1A_5) in Wolbachia Pipientis (WPip)." *Molecular Ecology Resources* 11(4):753-56.

Pritchard, Leighton, Rachel H. Glover, Sonia Humphris, John G. Elphinstone, and Ian K. Toth. 2016. "Genomics and Taxonomy in Diagnostics for Food Security: Soft-Rotting Enterobacterial Plant Pathogens." *Anal. Methods* 8(1):12-24. Retrieved (http://xlink.rsc.org/?DOI=C5AY02550H).

Rasgon, Jason L., Courtney E. Gamston, and Xiaoxia Ren. "Survival of Wolbachia pipientis in cell-free medium." Applied and environmental microbiology 72.11 (2006): 6934.

Riegler, Markus, Iñaki Iturbe-Ormaetxe, Megan Woolfit, Wolfgang J. Miller, and Scott L. O'Neill. 2012. "Tandem Repeat Markers as Novel Diagnostic Tools for High Resolution Fingerprinting of Wolbachia." *BMC Microbiology* 12(Suppl. 1):S12. Retrieved (http://www.biomedcentral.com/1471-2180/12/S1/S12).

Salzberg, Steven L., Daniela Puiu, Daniel D. Sommer, Vish Nene, and Norman H. Lee. 2009. "Genome Sequence of the Wolbachia Endosymbiont of Culex Quinquefasciatus JHB." *Journal of Bacteriology* 191(5):1725.

Sanogo, Yibayiri O. and Stephen L. Dobson. 2006. "WO Bacteriophage Transcription in Wolbachia-Infected Culex Pipiens." *Insect Biochemistry and Molecular Biology* 36(1):80-85.

Serbus, Laura R. and William Sullivan. 2007. "A Cellular Basis for Wolbachia Recruitment to the Host Germline." *PLoS Pathogens* 3(12):1930-37.

Shao, Yucheng et al. 2011. "Tadb: A Web-Based Resource for Type 2 Toxin-Antitoxin Loci in Bacteria and Archaea." *Nucleic Acids Research* 39(Suppl. 1):606-11.

Shen, Xiaodong et al. 2012. "Functional Identification of the DNA Packaging Terminase from Pseudomonas Aeruginosa Phage PaP3." *Archives of Virology* 157(11):2133-41.

Shragai, Talya, Blanka Tesla, Courtney Murdock, and Laura C. Harrington. 2017. "Zika and Chikungunya: Mosquito-Borne Viruses in a Changing World." *Annals of the New York Academy of Sciences* 1399(1):61-77.

Shropshire, J. Dylan, Jungmin On, Emily M. Layton, Helen Zhou, and Seth R. Bordenstein. 2018. "A Single Prophage WO Gene Rescues Cytoplasmic Incompatibility in *Drosophila melanogaster*." *BioRxiv* (21):300269. Retrieved (https://www.biorxiv.org/content/early/2018/04/U.S. Appl. No. 13/300,269).

Singhal, Kopal and Sujata Mohanty. 2018. "Comparative Genomics Reveals the Presence of Putative Toxin—Antitoxin System in Wolbachia Genomes." *Molecular Genetics and Genomics* 293(2):525-40. Retrieved (http://dx.doi.org/10.1007/s00438-017-1402-5).

Siozios, Stefanos et al. 2013. "Draft Genome Sequence of The." *Genome Annuncements* 1(1):e00032-13.

Sun, Ling V et al. 2001. "Determination of *Wolbachia* Genome Size by Pulsed-Field Gel Electrophoresis." *Journal of Bacteriology* 183(7):2219-25.

Tatusov, Roman L., Michael Y. Galperin, Darren A. Natale, and Eugene V Koonin. 2000. "The COG Database: A Tool for Genome-Scale Analysis of Protein Functions and Evolution." *Nucleic Acids Research* 28(1):33-36. Retrieved (http://www.ncbi.nlm.nih.gov/pmc/articles/PMC102395/).

Teixeira, Luís, Álvaro Ferreira, and Michael Ashburner. 2008. "The Bacterial Symbiont Wolbachia Induces Resistance to RNA Viral Infections in Drosophila Melanogaster." *PLoS Biology* 6(12):2753-63.

Turelli, Michael and Ary A. Hoffmann. 1991. "Rapid Spread of an Inherited Incompatibility Factor in California Drosophila." *Nature* 353(6343):440-42. Retrieved (http://www.nature.com/doifinder/10.1038/353440a0).

Turelli, Michael. 1994. "Evolution of Incompatibility-Inducing." 48(5):1500-1513.

(56) References Cited

OTHER PUBLICATIONS

Werren, J. H. and D. M. Windsor. 2000. "Wolbachia Infection Frequencies in Insects: Evidence of a Global Equilibrium?" *Proceedings of the Royal Society B: Biological Sciences* 267(1450):1277-85. Retrieved (http://rspb.royalsocietypublishing.org/cgi/doi/10.1098/rspb.2000.1139).
Werren, John H. 1997. "Biology of Wolbachia." *Annu. Rev. Entomol.* 124(42):587-609.
Wood, David O. et al. 2012. "Establishment of a Replicating Plasmid in Rickettsia Prowazekii." PLoS ONE 7(4):1-6.
Woolfit, Megan et al. 2013. "Genomic Evolution of the Pathogenic Wolbachia Strain, WMelPop." Genome Biology and Evolution 5(11):2189-2204.
Wright, John D., Fritiof S. Sjostrand, Joseph K. Portaro, and A. Ralph Barr. 1978. "The Ultrastructure of the Rickettsia-like Microorganism Wolbachia Pipientis and Associated Virus-like Bodies in the Mosquito Culex Pipiens." Journal of Ultrasructure Research 63(1):79-85.
Zimmermann, Lukas et al. 2018. "A Completely Reimplemented MPI Bioinformatics Toolkit with a New HHpred Server at Its Core." Journal of Molecular Biology 430(15):2237-43. Retrieved (http://www.sciencedirect.com/science/article/pii/S0022283617305879).

* cited by examiner

| | Num VNTRs | Location | Individual hosts | Accession |
|---|---|---|---|---|
| Culex 003 | 7 | France | Single | This study |
| Culex 007 | 5 | France | Single | This study |
| Culex 011 | 6 | France | Single | This study |
| Culex 012 | 6 | France | Single | This study |
| Culex mpU5[1] | 6.5 | U.S.A | Single | GU563802.1 |
| Culex mpGR[1] | 7 | Greece | Single | GU583796.1 |
| Culex mpAU[1] | 7 | Australia | Single | GU583799.1 |
| Culex mpJP[1] | 11.5 | Japan | Single | GU583800.1 |
| Culex mpIT[1] | 15.5 | Italy | Single | GU583797.1 |
| Culex JHB[2] | 7 | S. Africa Lab Line | Multiple | GU583802.1 |
| Culex Molestus[3] | 13.5 | Italy Lab Line | Multiple | GU563802.1 |

ParA-like gene Variable number tandem repeat (VNTR) Hypothetical protein

[1]Petridis, M. and Chatzidimitriou, D. (2011) doi:10.1111/j.1755-0998.2011.02981.x, [2]Salzberg, S. L. et al. (2009) doi:10.1127/JB.01731-08, [3]Pinto, S. B. et al. (2013) doi:10.1371/journal.ppat.1003647

FIG. 5

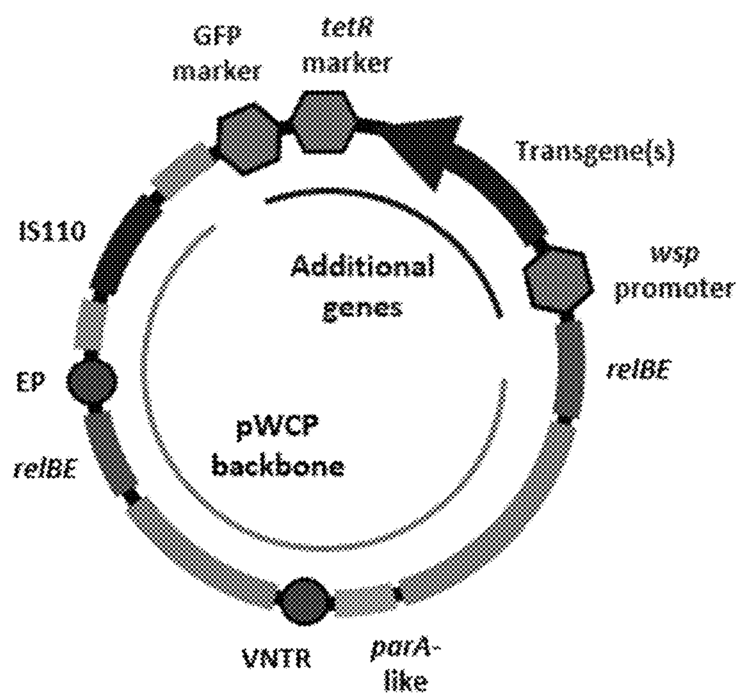

FIG. 6

(a) Long-reads that cover more than 50% of pWCP
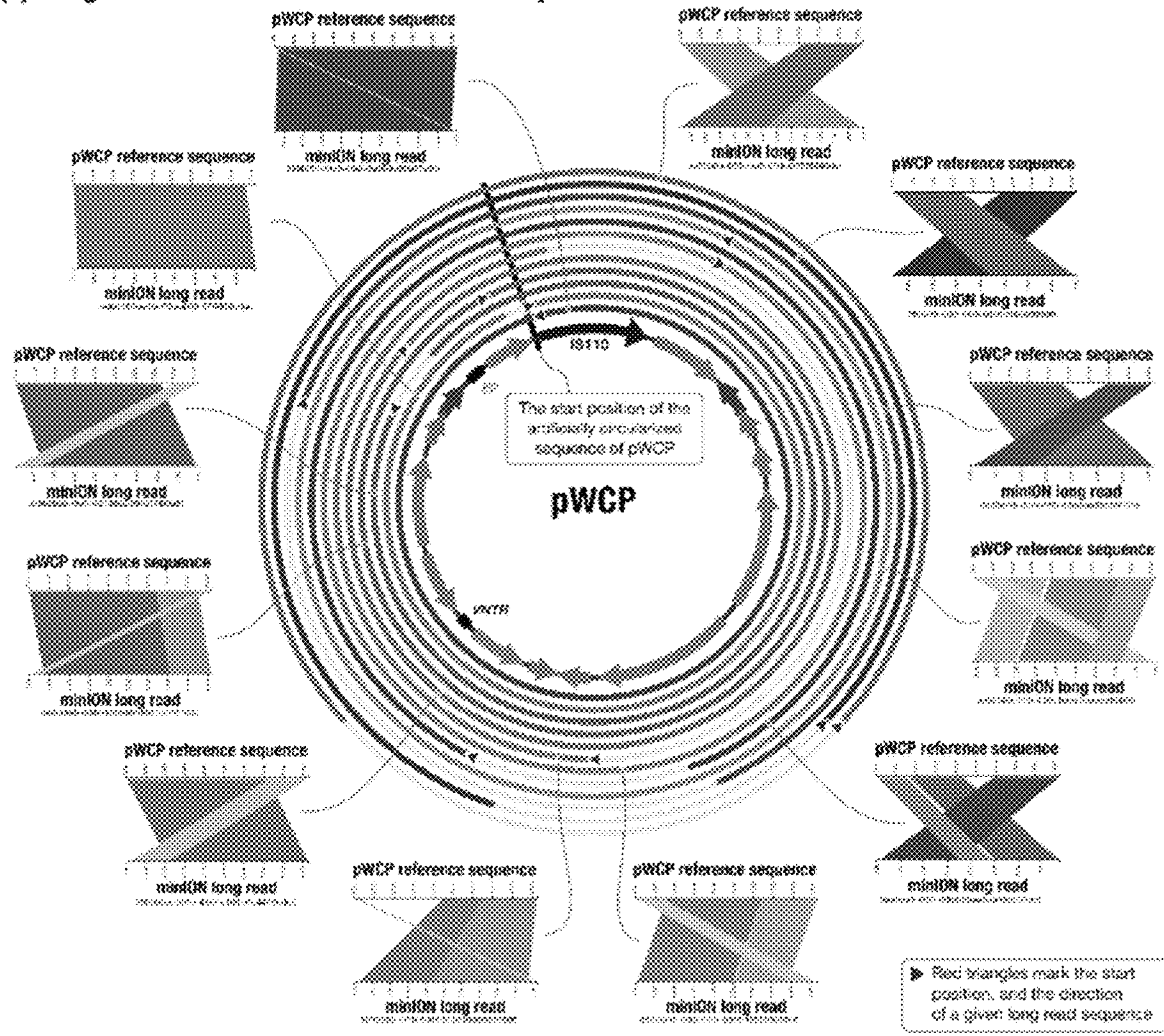
(b) Long-reads that cover less than 50% of pWCP
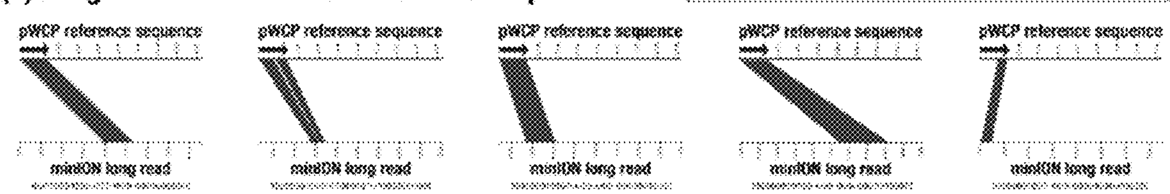
FIG. 9

SEQUENCE LISTING

<160> NUMBER OF SEQ ID NOS: 19

<210> SEQ ID NO 1
<211> LENGTH: 948
<212> TYPE: DNA
<213> ORGANISM: Artificial Sequence
<220> FEATURE:
<223> OTHER INFORMATION: Synthetic construct

<400> SEQUENCE: 1

```
atgattacat cttatcaaaa ttttattggc attgatatcg ggaaatttaa aaatgttgtt     60
gcagttcacg aacagaagaa tactgtagga tttgacaata atacttctgg ctggcaacaa    120
ttgtttcaaa agttttcaga tatcctacct aattctttag taactttaga aaatacagga    180
aagtatgagc ttggtttatt acattttctt gttgacaaaa atattgccac acatcgagct    240
aatacccgta aagtaaaaag ctttatcttg tctcacggaa ctttagcaaa gtctgataaa    300
tcagatgcaa gagctcttgc tcaatatgga tttgaacgcc acagcactat ctctctattt    360
gtacccactt ttgaaaatca atcaaccttg gttgcacttt gtcaacgtcg tgatgacatt    420
acgcaaatga gagctcagga aaaatgtaga ctggcagcac ctgaaaatga ccatataaaa    480
gaaagttgtc aaaaaactat cgaattcttt aatattcaaa tagatgaact caataatact    540
atacaaaaaa ttattgatga aagccgtgag ttacaacaac gtcaaaaaat cctaaaaaca    600
gttcctggaa taggtccaaa gttatctcaa gattttctct gtttaatgcc agagcttggt    660
tacttaagca ggagagaagt tgcaagcctt gctggggttg caccttatcc aaaagaaagt    720
ggtaaaacta ttggataccg aagaataaca ggtggtagaa gcaatgttcg tgcaaaactt    780
tttacatctg ccatggctgc tgcaaagtcc aaatctgtac ttggtgcctt ttattctaag    840
cttgttgaaa gtggtaagaa gaagatggta gctataacag ctctaatgcg taaaattata    900
gtaattgcta acgcaaggct taaagaagca attaatttga atatttaa                 948
```

<210> SEQ ID NO 2
<211> LENGTH: 315
<212> TYPE: PRT
<213> ORGANISM: Artificial Sequence
<220> FEATURE:
<223> OTHER INFORMATION: Synthetic construct

<400> SEQUENCE: 2

```
Met Ile Thr Ser Tyr Gln Asn Phe Ile Gly Ile Asp Ile Gly Lys Phe
1               5                   10                  15

Lys Asn Val Val Ala Val His Glu Gln Lys Asn Thr Val Gly Phe Asp
            20                  25                  30

Asn Asn Thr Ser Gly Trp Gln Gln Leu Phe Gln Lys Phe Ser Asp Ile
        35                  40                  45

Leu Pro Asn Ser Leu Val Thr Leu Glu Asn Thr Gly Lys Tyr Glu Leu
    50                  55                  60

Gly Leu Leu His Phe Leu Val Asp Lys Asn Ile Ala Thr His Arg Ala
65                  70                  75                  80

Asn Thr Arg Lys Val Lys Ser Phe Ile Leu Ser His Gly Thr Leu Ala
                85                  90                  95

Lys Ser Asp Lys Ser Asp Ala Arg Ala Leu Ala Gln Tyr Gly Phe Glu
            100                 105                 110

Arg His Ser Thr Ile Ser Leu Phe Val Pro Thr Phe Glu Asn Gln Ser
        115                 120                 125

Thr Leu Val Ala Leu Cys Gln Arg Arg Asp Asp Ile Thr Gln Met Arg
    130                 135                 140

Ala Gln Glu Lys Cys Arg Leu Ala Ala Pro Glu Asn Asp His Ile Lys
145                 150                 155                 160

Glu Ser Cys Gln Lys Thr Ile Glu Phe Phe Asn Ile Gln Ile Asp Glu
                165                 170                 175

Leu Asn Asn Thr Ile Gln Lys Ile Ile Asp Glu Ser Arg Glu Leu Gln
            180                 185                 190
```

```
Gln Arg Gln Lys Ile Leu Lys Thr Val Pro Gly Ile Gly Pro Lys Leu
        195                 200                 205

Ser Gln Asp Phe Leu Cys Leu Met Pro Glu Leu Gly Tyr Leu Ser Arg
    210                 215                 220

Arg Glu Val Ala Ser Leu Ala Gly Val Ala Pro Tyr Pro Lys Glu Ser
225                 230                 235                 240

Gly Lys Thr Ile Gly Tyr Arg Arg Ile Thr Gly Gly Arg Ser Asn Val
                245                 250                 255

Arg Ala Lys Leu Phe Thr Ser Ala Met Ala Ala Ala Lys Ser Lys Ser
            260                 265                 270

Val Leu Gly Ala Phe Tyr Ser Lys Leu Val Glu Ser Gly Lys Lys Lys
        275                 280                 285

Met Val Ala Ile Thr Ala Leu Met Arg Lys Ile Ile Val Ile Ala Asn
    290                 295                 300

Ala Arg Leu Lys Glu Ala Ile Asn Leu Asn Ile
305                 310                 315


<210> SEQ ID NO 3
<211> LENGTH: 9228
<212> TYPE: DNA
<213> ORGANISM: Artificial Sequence
<220> FEATURE:
<223> OTHER INFORMATION: Synthetic construct

<400> SEQUENCE: 3

aatattgtaa gtcaaaaata tgatataaag gaaataagag ggaaagataa ccctactcac      60

tataggaata gggttatcac gggcgtgtgc gaccggcaga atattggtat tacaaccgtg     120

tccatcaagg tacactagcc catctctcga tacgtttgaa tagttgtgtg ggacatgtat     180

atgcacccgt ttacaatctt aaattaatta aactatcgag gttataatga ttacatctta     240

tcaaaatttt attggcattg atatcgggaa atttaaaaat gttgttgcag ttcacgaaca     300

gaagaatact gtaggatttg acaataatac ttctggctgg caacaattgt ttcaaaagtt     360

ttcagatatc ctacctaatt ctttagtaac tttagaaaat acaggaaagt atgagcttgg     420

tttattacat tttcttgttg acaaaaatat tgccacacat cgagctaata cccgtaaagt     480

aaaaagcttt atcttgtctc acggaacttt agcaaagtct gataaatcag atgcaagagc     540

tcttgctcaa tatggatttg aacgccacag cactatctct ctatttgtac ccacttttga     600

aaatcaatca accttggttg cactttgtca acgtcgtgat gacattacgc aaatgagagc     660

tcaggaaaaa tgtagactgg cagcacctga aaatgaccat ataaaagaaa gttgtcaaaa     720

aactatcgaa ttctttaata ttcaaataga tgaactcaat aatactatac aaaaaattat     780

tgatgaaagc cgtgagttac aacaacgtca aaaaatccta aaaacagttc ctggaatagg     840

tccaaagtta tctcaagatt ttctctgttt aatgccagag cttggttact taagcaggag     900

agaagttgca agccttgctg ggttgcacc ttatccaaaa gaaagtggta aaactattgg     960

ataccgaaga ataacaggtg gtagaagcaa tgttcgtgca aaacttttta catctgccat    1020

ggctgctgca aagtccaaat ctgtacttgg tgccttttat tctaagcttg ttgaaagtgg    1080

taagaagaag atggtagcta taacagctct aatgcgtaaa attatagtaa ttgctaacgc    1140

aaggcttaaa gaagcaatta atttgaatat ttaaaattta catagcagta attgaaatga    1200

atattgtgaa taagcacgtc cgcacaaact taaagtgctt attcacaata gcttaaacgg    1260

aaattgttgc agcagctgtt tgatatagaa ttctgtttct atgacaaacg ggtttttatt    1320
```

-continued

```
atctatatgg ttgggtaaag ttgcaaaatt atacaaataa aaaatttaaa aaacatagtt   1380

gatggagctt ctctaccaag gattaaatga attagccttt ttaaatctcc ttgtcgatag   1440

ttcaggaagt atggatttaa atgtgctgag aagaaagatt gcatcaatct gtgaaaaaca   1500

cagcatcaaa tgcatctaca ttgactatct gcagctactc agaggatcag gaagaacaga   1560

gaacagaacg cttgaagtga cagaaatcag cagaacatta aagaacatcg ctaaagactt   1620

tgcagttcct gttgtcgcgc tatcacaaat tagtcgcaga gtggaagaaa ggcaaaacaa   1680

aagaccgcaa ctagcagacc tgcgagagtc agggagcatc gaacaagacg ctgatatagt   1740

tttactactc tacagagaca gctactataa gataggctct aataacgaac tagagataaa   1800

tgtcgcaaag aatagaagtg gctcaaccgg taaagttaca gtgcgctatc aagttaatac   1860

tggaagaata ttgatttaac gttttagtaa gtctaatatt gcctgattgt aaatgttatc   1920

tctatgtcct attgagacaa cagttactat acgttttgca gtatctacac ggtagacgat   1980

acgataatca cccactcgta ttctgcgata tccctttaat ctattgcgta atgatacacc   2040

gctagcaata ggatcagtct caagatattc ttttattgct tctttaatac ttggtttaat   2100

gtcttctggt aaggaaggta tattcctctt aataacatgt ttgagatatt tgatagtata   2160

acgtttattt ccagatgtct tcactatctt ctatttcttc cgcatcatca tcacttaatt   2220

ctctaataat tttagaaaac gcaatgtctt ctgcttcaag ctcaattgct tctttgacta   2280

actttcctgc taatttttga acagactgct tggtagcttt agctagttca ataaggtgct   2340

gtgaagtttc tgtatcgaag gttacattaa tccttgaatc tgccataagt tttaccaaag   2400

tttatcagta attatataat attttcctga atttttcaat aaagatctct cctaaactta   2460

gaagagatct ttatggttaa actactttga tttgctcgaa gtctgtaaag caaagtatgt   2520

gcttgaattc acgaacgaag aaggtaatga accccctaac tgttctagct ctctcagaga   2580

aagcttccct tccataacac accttgcgtt tttctcttct tgtgtctcag aaattttttg   2640

attatacttt gaacacgagg cactctcatc atttctttta aaatctttca taattaatcc   2700

cttaaagcta taaaaaatac taaactagta tacagtaaaa cataatactt tagcaagtta   2760

ctatcccagt tgatttagtg ttttctcaga tattaaacct ttttttagta ataatgtatt   2820

tttcacttct cttaaatctg tagaaggacc tccaagttga tccacaactt ctgaaatatc   2880

ccatttagtc ggatctggca tatgcggtaa aagccttccc catgaacctc ctaattgctc   2940

taactctttt tcaggatatt tttcctgctg cacctgtgag cccaattctt taagtgcaaa   3000

ccttgcctct ggactttttg ctataaaatc ctctacttta ttagctcctt cagataaaag   3060

ctttacctcc tcagaacttt cttgttgcaa ttgtgacgct aacgcttcat acaaaggctt   3120

tgctttacct tgaggaccta atattacctc tgtatttgct tgcaactgtt cttcagtaat   3180

accatttctt tcaataaact cgacaggctt gtcagaatga ataagaactt tgatcttaca   3240

ttcttttcct tcaacttccc aattaatagt catttcatat gaatcatgag ctacctcata   3300

tattcttgtt ccatcctcac aaagggacaa acgtattcct ctcgttttat tatcgtcagg   3360

agagcaaaga gtaattgttg taatacctag ttcattgcat gatttaccac tcaaaaagtc   3420

tagcaagttg atttcttttt taccttcaag ccactcaagc cttatggaag gaaaagcaac   3480

tccatcttca tctacatgtt tttcaagaca taaaaaattt agttttaaac cgctatcttt   3540

tatttttctt aatacttctt ttttcgtttc atctgtaaca aatcctgtaa ttataggtcg   3600

ttcacgataa ttcatatcat acaatttgcc attgcccagc atatcagcat gaaaataatc   3660

agaagaaaat ttctcccacg aatccttatc tgaaaagtga tggccatgtg tattaccagg   3720
```

-continued

```
aataaaatca cttacagaat ttctactaaa acccttatca agaaaaagtg gaactaaagt   3780
ttccccaaac ttctttttac ttgaccaaat cgattttctt aaagcattta acatactaac   3840
ccccatatta atgccataat aaatttatta tgacattacg gaatatgcta agtcaagttt   3900
ataactttaa atttttatga aaattaacaa aaaaatcata ctttacatgg catgaaaaac   3960
gccgtattat accacctcta gtagaaatca agcttaaaat ttaagggaat ttgcgtaaag   4020
ggcatttctg ccctttacac gcatttaaat ttttagtaga ttcgagctgc aaacaaaaaa   4080
tcttactaag acacatgagg cacaaaaaca acagaacgta tcgcaccaga acgtatcaaa   4140
aaaaattgta cagaaacgaa aaaaagagtc aagcaaaaaa aagcttgact tcccattatc   4200
gcgtctatca caacttcagc ataagaggaa gccttcatat agttaacgta aacggtaaat   4260
atgtgcaggc gcaaataggc tctagaaggc gaataaaggc gcgagaaaag tcaattgagc   4320
ttaagcgtcc gataagaact ttcgacacgc gtcttactgg cagtgaacta ctacaagttt   4380
taaaaaacaa ggaagtaaga tggtttaaaa acggcactgc tgttcctccg gaacatagta   4440
cttatctttt agaggctttt aatccacaca aagcaaagaa aatcttttcc agttcagcgc   4500
aaaaagcggc ggaaaaatac tttgtcagag tagtaaaaga aaaatttcgc gatttaaaaa   4560
cagcgaaagc accggatgtg ctcgcaatta gagagaaagc agtagaaaaa gttctcgaaa   4620
agttcaagaa tcactgtgaa tttatatcaa tagaggtata cattaagaac ttatggataa   4680
ctttcgacga acatctctat agcaagatga gcatgaaaga aaaagtggac caccacatcg   4740
atttgatcat acaaaacact agtcaggaga gagaggaaga actgcttgct gcaggagaaa   4800
cgccggagga agtataccac actttcagaa cggtccaggg atcgaatctg tatcgcatca   4860
ggctgctgag cgagcgagga ggagctgcgc ttgagatata catcaggaaa gagctgcagc   4920
ggcggctaaa actccttttc aaccacttta aagatagaat gatcagaatt ggtgtcgaca   4980
cggagaaaga ctttttctcg attgcccgcc ggcatttttc gtttttattc acgaagaaat   5040
acgtcaaaaa cagaaagaaa gtgatgaggg aggtacgtca tatccttgct ctcatcagag   5100
aaaacccgtt tgatgttctg aaggattacg acaatttatg caaatttgat ccaccacctc   5160
tctagagaaa gcaaaaatgt tacccgaaag tgacccccat catgcttaat tgaaaaaaac   5220
aataaaaagt gcgacgatta tattagtttt agtattagga aattgctctt acttaaaaaa   5280
taataaggta aaatcctttc atttttcttt ctatttaaaa aagttataca caatacaata   5340
tataaaagta tatattatag tttttatagt atattcttat tataaaagtc gaaagtaccc   5400
ctatattatc actataaagg aagaaagagt tatagagagg ttattcacag ttatttcttc   5460
aaagttttaa tgtattcagt taaagccctg aatccaatgt tagagaccgt atcttgagtt   5520
ttaaaggcta tttctttcac ttctctacaa agatcaggtg aaagccttaa tgttaatcgt   5580
tgtttttgtt cccgttcttt aataaaagca tgtctctgtt gatcctcttt tttataaccc   5640
acatcagaga ttctatgtaa tctatgttcc ttcgatctat gttctgaaat tacaggcatt   5700
attattttct tagtgtccac taaaaacctc cttgtaaata gatttaattt cctcaattgc   5760
ctttgaatcg gctgattcaa caatcgtcaa accttcaaga gaggagtctt caactacagc   5820
ccgctgactc aaaaaactat cgagccttgt taaattatca aaatgactta gaaaactatc   5880
acattttgtg attatttttt tagctctagt tggattagta ttaactcgat taagtaggat   5940
tcttgcttta aagattttat tacaactccg agcaccggca attaaattgt taagaacttt   6000
gaatgtccac acatcaattc cagatggaac aatcggaaag atcactatat cagctagtaa   6060
```

```
taaagcagct cttaatgctt cattattacc accacctaca tcaacaacaa tgtcttgata   6120
ttcagaatgc aaagctgtta gttcattttt gattgctatg ccatctcgtg gcccttgact   6180
actgctaatc accggtaagt ttatgtcctg atctcgttga gatgcccaca agctggccat   6240
ctcttgatga tcaatatcat agaggtgaac gtttctacct tctagagtac gcattaatgc   6300
tatgtttgtg gctatggttg ttttaccaca accacctttc tgaccaccga ctaatattat   6360
catgcctacc ttagttataa aacaacatct tagtgacacg tcaccatgtc gtcaagtcaa   6420
cgtgtcacta tgtcaacgtg tcaccatgtc aacgtgtcaa cgtgtcacca tgtcaccatg   6480
tcaccatgtc gcaaacaagg cttattcact gaataatcaa caattctgtt aataactaca   6540
aacactcaag caagaaaaag gagcttttgc tcgcacagaa acatcgtttt tagcgtcgtt   6600
cttcaaaatc gtataattat acacgttatc ggggcaaggt atccctagac ggtttctttc   6660
aggaaaccac atgatgaact cactgaggac atcggcgata tcatcggtga actcagtttc   6720
agtatgaatc ttttcaaact catcaaatat caaataatga aaatctcttt ccgctttctc   6780
aagaaagata tgaccttgct caacaaactg actgcaagac tgaaacactt ccatctttga   6840
cctcgttctt cttgagccta aaatcagtgt gtctggcaat agcattcgaa gatctgcgat   6900
caccttaaag ccaataccgt gttcttccac gactactgcg tgcagcctat gctcatattt   6960
actgagaaac tcatgaatat cgtgttcaac tgaactcggg tcaagctttc ttgccaataa   7020
atccacccat actccacatc tttttggctg atgggcaaaa tcactcttcg taaagaacgg   7080
ctgaaacact cctaccgctg ttctatcaag tgttttcagc gaaccactgt tgagatcgat   7140
aaatgctacc agatcttttt ctcctatttt ctcataagga aaatcaatat tcctaataat   7200
gtcttgcaat actatactta gtattaactt ctgtgtcatt tctcccgagc atcagcaaaa   7260
gccaatgact ctgtatactc aacctaccat aatctgtcaa cataattctt tattgaaaat   7320
ttattaacac aggttgagta tttttcaatt atatctataa taaaaagatg gatatgaaat   7380
accgttattg ggactctcca gaaacagaag agattgttcg caaaacttac gatgctcaat   7440
taaagattat agatgatata aaaaatgata aagaacttgg gaaattagca ttagaaatat   7500
tatataccgt tacttactgt aatttacggg atcttccctt attaactttt tatagttcag   7560
ctaccacaca tcataataat ctttatggtg gtgtggatct tcatacactt tatgaacttt   7620
atgatgaacc ttttgaagat gctgaagatt tactaatggc ttcttttgat ttattagtaa   7680
aatatcaatt ggttgattgt tataaaaatg gagtgataca agtgttatcc atgcatcaag   7740
tcactcgaag caatatacag cttatgttaa aagaacaagg tatagaagaa gaagttttaa   7800
aaaaagccat aagtgtatta tcgagatttc tgagtgagct caaatattca ttagatgaca   7860
aggatgaagg agcgggtttt ttttctttca tagaaggaat aattccgtat gcgtgctcta   7920
atgcacaaca cgttttatat catgcagagg aatacaaaga attaaataag tattgcgaaa   7980
aagaaaaatt agaactttta attgattatt tcgtagcagc aagactttat caaaaacata   8040
gtattactat acatcactaa atattaaata tattttatac agccctcctt cctcttcacc   8100
ttaacaattc tttattgaaa atttcatgaa aatgttgtat aattgtagag tagtagaact   8160
cggtaaaact catggcaaac gctaatttag ctttcagtaa agaaacttta cagcatcttg   8220
ctgaattatc tgaacttact aagcaacctg ctcaagcatt agcagaaaaa ctacttaaag   8280
aagcaatcga gcttgaaatc gaagattttt tagtttctaa aatttctgat gagcgtgatg   8340
tcgaaggtgc agaaatgatt aaaagtgagg atgtagattg ggatacacta ttatcttcgt   8400
aggaaaggtt attagaaaag accttcctga ccttccaaaa acaataagat tgagggtcgt   8460
```

```
aaatgcgata aatgaaagac ttacagttga tccaatgaac ctcggtgaac cattgcacca   8520

cagcttaaaa ggacgtagaa ggttaagagt tggtgagtac cgtgtgattt acagagtaaa   8580

tcaattagaa caaatagtga ccatcacaga gataggacat agatgtgata tttataaaaa   8640

ataaatataa acattaaata tacattatac agcccttctt cctgatccat tcttcacctt   8700

aggcggcttt gctcagctca aaaataacta ttttttggg taccccccac tataagttat   8760

attatattat attatttata tataatataa tataactcat tgggagaggc gacgaaaaca   8820

agatcttgag tttgaggagc ctccggtttt aggtgaagaa tggatcagga agaagggctc   8880

agggtcgatg aggacgtaag gccaatattt gattatctca aagactacag agactacatc   8940

gataaacggc tagcaaatcc cgacgaaata gaaggaataa ccacaggaat aaaggagctt   9000

gacacaataa caggtggctt caaggaagga gagctctctg tgcttgcagc acgcacctca   9060

attggcaaga cttcaatagc actacacatg gctctagagg ccgcaaagct cttaaatgac   9120

cacgagtatg tctgcttctt ctcccttgaa atgtcagcca atcaactcat caacagaata   9180

atcagcatca aagtcaatga gacagtcaac actatcatta aaaacaag               9228
```

```
<210> SEQ ID NO 4
<211> LENGTH: 654
<212> TYPE: DNA
<213> ORGANISM: Artificial Sequence
<220> FEATURE:
<223> OTHER INFORMATION: Synthetic construct

<400> SEQUENCE: 4

atgataatat tagtcggtgg tcagaaaggt ggttgtggta aaacaaccat agccacaaac     60

atagcattaa tgcgtactct agaaggtaga aacgttcacc tctatgatat tgatcatcaa    120

gagatggcca gcttgtgggc atctcaacga gatcaggaca taaacttacc ggtgattagc    180

agtagtcaag ggccacgaga tggcatagca atcaaaaatg aactaacagc tttgcattct    240

gaatatcaag acattgttgt tgatgtaggt ggtggtaata atgaagcatt aagagctgct    300

ttattactag ctgatatagt gatctttccg attgttccat ctggaattga tgtgtggaca    360

ttcaaagttc ttaacaattt aattgccggt gctcggagtt gtaataaaat ctttaaagca    420

agaatcctac ttaatcgagt taatactaat ccaactagag ctaaaaaaat aatcacaaaa    480

tgtgatagtt ttctaagtca ttttgataat ttaacaaggc tcgatagttt tttgagtcag    540

cgggctgtag ttgaagactc ctctcttgaa ggtttgacga ttgttgaatc agccgattca    600

aaggcaattg aggaaattaa atctatttac aaggaggttt ttagtggaca ctaa          654
```

```
<210> SEQ ID NO 5
<211> LENGTH: 523
<212> TYPE: DNA
<213> ORGANISM: Artificial Sequence
<220> FEATURE:
<223> OTHER INFORMATION: Synthetic construct

<400> SEQUENCE: 5

ttggtaaaac ttatggcaga ttcaaggatt aatgtaacct tcgatacaga aacttcacag     60

caccttattg aactagctaa agctaccaag cagtctgttc aaaaattagc aggaaagtta    120

gtcaaagaag caattgagct tgaagcagaa gacattgcgt tttctaaaat tattagagaa    180

ttaagtgatg atgatgcgga agaaatagaa gatagtgaag acatctggaa ataaacgtta    240

tactatcaaa tatctcaaac atgttattaa gaggaatata ccttccttac cagaagacat    300
```

taaaccaagt attaaagaag caataaaaga atatcttgag actgatccta ttgctagcgg 360
tgtatcatta cgcaatagat taaagggata tcgcagaata cgagtgggtg attatcgtat 420
cgtctaccgt gtagatactg caaaacgtat agtaactgtt gtctcaatag gacatagaga 480
taacatttac aatcaggcaa tattagactt actaaaacgt taa 523

<210> SEQ ID NO 6
<211> LENGTH: 473
<212> TYPE: DNA
<213> ORGANISM: Artificial Sequence
<220> FEATURE:
<223> OTHER INFORMATION: Synthetic construct

<400> SEQUENCE: 6
atggcaaacg ctaatttagc tttcagtaaa gaaactttac agcatcttgc tgaattatct 60
gaacttacta agcaacctgc tcaagcatta gcagaaaaac tacttaaaga agcaatcgag 120
cttgaaatcg aagatttttt agtttctaaa atttctgatg agcgtgatgt cgaaggtgca 180
gaaatgatta aaagtgagga tgtagattgg gatacactat tatcttcgta ggaaaggtta 240
ttagaaaaga ccttcctgac cttccaaaaa caataagatt gagggtcgta aatgcgataa 300
atgaaagact tacagttgat ccaatgaacc tcggtgaacc attgcaccac agcttaaaag 360
gacgtagaag gttaagagtt ggtgagtacc gtgtgattta cagagtaaat caattagaac 420
aaatagtgac catcacagag ataggacata gatgtgatat ttataaaaaa taa 473

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
ctagaggccg caaagctctt 20

<210> SEQ ID NO 8
<211> LENGTH: 20
<212> TYPE: DNA
<213> ORGANISM: Artificial Sequence
<220> FEATURE:
<223> OTHER INFORMATION: Synthetic construct

<400> SEQUENCE: 8
cgtcttgttc gatgctccct 20

<210> SEQ ID NO 9
<211> LENGTH: 21
<212> TYPE: DNA
<213> ORGANISM: Artificial Sequence
<220> FEATURE:
<223> OTHER INFORMATION: Synthetic construct

<400> SEQUENCE: 9
acacatcgag ctaatacccg t 21

<210> SEQ ID NO 10
<211> LENGTH: 22
<212> TYPE: DNA
<213> ORGANISM: Artificial Sequence
<220> FEATURE:
<223> OTHER INFORMATION: Synthetic construct

<400> SEQUENCE: 10
ccaagctctg gcattaaaca ga 22

<210> SEQ ID NO 11
<211> LENGTH: 25
<212> TYPE: DNA
<213> ORGANISM: Artificial Sequence
<220> FEATURE:
<223> OTHER INFORMATION: Synthetic construct

<400> SEQUENCE: 11
ggtcaacaaa tcataaagat attgg 25

<210> SEQ ID NO 12
<211> LENGTH: 26
<212> TYPE: DNA
<213> ORGANISM: Artificial Sequence
<220> FEATURE:
<223> OTHER INFORMATION: Synthetic construct

<400> SEQUENCE: 12
taaacttcag ggtgaccaaa aaatca 26

<210> SEQ ID NO 13
<211> LENGTH: 21
<212> TYPE: DNA
<213> ORGANISM: Artificial Sequence
<220> FEATURE:
<223> OTHER INFORMATION: Synthetic construct

<400> SEQUENCE: 13
catacctatt cgaagggata g 21

<210> SEQ ID NO 14
<211> LENGTH: 21
<212> TYPE: DNA
<213> ORGANISM: Artificial Sequence
<220> FEATURE:
<223> OTHER INFORMATION: Synthetic construct

<400> SEQUENCE: 14
agcttcgagt gaaaccaatt c 21

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
cgtcttgttc gatgctccct 20

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
ctagaggccg caaagctctt 20

<210> SEQ ID NO 17
<211> LENGTH: 36
<212> TYPE: DNA

```
<213> ORGANISM: Artificial Sequence
<220> FEATURE:
<223> OTHER INFORMATION: Synthetic construct

<400> SEQUENCE: 17

gcctacctta gttataaaac aacatcttag tgacac                              36


<210> SEQ ID NO 18
<211> LENGTH: 33
<212> TYPE: DNA
<213> ORGANISM: Artificial Sequence
<220> FEATURE:
<223> OTHER INFORMATION: Synthetic construct

<400> SEQUENCE: 18

caaggcttat tcactgaata atcaacaatt ctg                                 33


<210> SEQ ID NO 19
<211> LENGTH: 209
<212> TYPE: DNA
<213> ORGANISM: Artificial Sequence
<220> FEATURE:
<223> OTHER INFORMATION: Synthetic construct

<400> SEQUENCE: 19

agcccttctt cctgatccat tcttcacctt aggcggcttt gctcagctca aaaataacta     60

tttttttggg taccccccac tataagttat attatattat attatttata tataatataa    120

tataactcat tgggagaggc gacgaaaaca agatcttgag tttgaggagc ctccggtttt    180

aggtgaagaa tggatcagga agaagggct                                      209
```

PLASMIDS FOR MANIPULATION OF *WOLBACHIA*

CROSS REFERENCE TO RELATED APPLICATIONS

This application is a national stage application filed under 35 U.S.C. § 371 of PCT/US2019/061611 filed Nov. 15, 2019, which claims the benefit of U.S. Provisional Patent Application Ser. No. 62/768,165 filed Nov. 16, 2018 and U.S. Provisional Patent Application Ser. No. 62/811,131 filed Feb. 27, 2019, which are expressly incorporated herein by reference.

STATEMENT REGARDING FEDERALLY SPONSORED RESEARCH

This invention was made with government support under Grant Nos. R01 AI132581 and R21 HD086833 awarded by the National Institutes of Health and Grant No. IOS 1456778 made by the National Science Foundation. The government has certain rights in the invention.

FIELD

The present disclosure relates to plasmids, systems, and methods for the transformation of *Wolbachia.*

BACKGROUND

Mosquitoes are major vectors of disease-causing pathogens worldwide including viruses such as dengue, West Nile, Chikungunya, Zika, and yellow fever. In the absence of effective vaccines and mosquito control strategies concomitant to a deleterious use of insecticides, novel vector biocontrol efforts are the focus of current study.

Over the last decade, the widely distributed endosymbiotic alpha-proteobacteria *Wolbachia* in arthropods has gained attention not only as a reproductive parasite that spreads itself at the expense of host fitness, but also as a new tool to control the transmission of diseases due to its capacity to block virus transmission and to manipulate host reproduction. Native *Wolbachia* reduce viral replication in the fruit fly *Drosophila*, and *Wolbachia* transinfections in mosquito species (i.e., *Aedes aegypti*, Ae. *albopictus*, Ae. *polynesienses* and *Anopheles stephensi*) result in pathogen-refractory mosquito lines.

*Wolbachia* is transovarially transmitted from the mother to offspring. In some arthropods, *Wolbachia* 'modifies' sperm in testes, which leads to embryonic lethality if the infected male mates with an uninfected female. When both male and female are infected with the same *Wolbachia* strain, the modification is 'rescued', and the compatibility is restored. However, if the male and female are infected by *Wolbachia* populations with different 'modification-rescue' systems, it results in a bi-directional incompatibility. This alteration, termed 'cytoplasmic incompatibility' (CI), is the most common *Wolbachia*-induced reproductive manipulation and can lead to population replacement by *Wolbachia*-infected strains. The 'Two-by-One' model describes the genetic basis of CI whereby two genes, cytoplasmic incompatibility factors cifA and cifB are required to induce CI, and one of the same genes, cifA, rescues CI in the fertilized embryo. These genes are located in the eukaryotic association module of *Wolbachia*'s phage WO that exhibits a temperate lifecycle, laterally transfers between *Wolbachia* coinfections, and evolves rapidly with frequent insertion/deletion events. Phage WO genes underpin *Wolbachia*'s ability to hijack sperm and egg via CI, and variation in these genes may account for phenotypic variation in CI within various insects species. These recent observations emphasize the importance of investigating genetic structures beyond the *Wolbachia* bacterial chromosome to study the complex interplay between arthropods and their endosymbionts.

While recent studies shed light on phage WO's roles in *Wolbachia* genome evolution and CI, other extrachromosomal elements, such as plasmids, have not been detected in *Wolbachia*. Thus, what is needed, are novel plasmids and methods of using these plasmids in methods for transforming *Wolbachia.*

The plasmids, systems, and methods disclosed herein address these and other needs.

SUMMARY

Disclosed herein are plasmids and systems for use in methods of transforming *Wolbachia*. The inventors have identified, for the first time, extrachromosomal plasmids within *Wolbachia*. Thus, the plasmids disclosed herein provide a method for the transformation of a *Wolbachia* cell, an organism that has been refractory to genetic manipulation techniques commonly used in other model organisms.

In some aspects, disclosed herein is a non-naturally occurring plasmid comprising a first nucleic acid sequence capable of transforming a *Wolbachia* cell. In some embodiments, the plasmid further comprises a second nucleic acid sequence, wherein the second nucleic acid sequence is a heterologous nucleic acid sequence.

In some embodiments, the first nucleic acid sequence comprises a gene encoding a transposase. In some embodiments, the transposase is selected from a member of the IS110 transposase family.

In some embodiments, the transposase is encoded by SEQ ID NO: 1. In some embodiments, the transposase sequence comprises SEQ ID NO:2.

In some embodiments, the first nucleic acid sequence comprises SEQ ID NO:3.

In some embodiments, the first nucleic acid sequence comprises a ParA-like gene. In some embodiments, the ParA-like gene comprises SEQ ID NO:4.

In some embodiments, the first nucleic acid sequence comprises a RelBE toxin-antitoxin operon. In some embodiments, the RelBE toxin-antitoxin operon comprises SEQ ID NO:5 or SEQ ID NO: 6.

In some embodiments, the plasmid further comprises a selectable marker. In some embodiments, the selectable marker comprises an antibiotic resistance marker. In some embodiments, the selectable marker comprises a tetracycline resistance marker. In some embodiments, the selectable marker comprises a green fluorescent protein (GFP) marker.

In some embodiments, the heterologous nucleic acid sequence comprises a heterologous gene. In some embodiments, the heterologous gene is operably linked to a promoter active in the *Wolbachia* cell. In some embodiments, the promoter is a *Wolbachia* surface protein (wsp) promoter. In some embodiments, the plasmid is an isolated plasmid or purified plasmid.

In some aspects, disclosed herein is a non-naturally occurring *Wolbachia* cell comprising one or more of the plasmids disclosed herein. In some embodiments, the cell is an isolated cell or purified cell.

In some aspects, disclosed herein is a method for transforming a *Wolbachia* cell, comprising introducing a non-naturally occurring plasmid into the cell, wherein the plasmid comprises a first nucleic acid sequence capable of transforming a *Wolbachia* cell. In some embodiments, the plasmid further comprises a second nucleic acid sequence, wherein the second nucleic acid sequence is a heterologous nucleic acid sequence.

BRIEF DESCRIPTION OF THE DRAWINGS

The accompanying figures, which are incorporated in and constitute a part of this specification, illustrate several aspects described below.

FIG. 5. Characterization of a variable number tandem repeat (VNTR) locus of pWCP.

FIG. 6. Schematic of a plasmid comprising pWCP backbone with transgene(s) and marker(s).

FIG. 9. Alignment of MinION long reads to pWCP. (a) The alignment of long reads that cover more than 50% of the pWCP genome (12 of 13 total long reads are shown). Each rectangular figure shows high scoring pairs (HSPs) and their alignments between pWCP and long reads. The broken HSPs that are parallel to each other are due to low quality regions in long read sequences, and they are shown in different shades. Concentric circles around pWCP demonstrate the alignment of each long read and their start and stop positions. (b) The alignment of long reads that cover less than 50% of the pWCP genome (only 5 of 6 are shown). Every long read shown in the figure has a hit to the IS110 TE.

DETAILED DESCRIPTION

Figure 1:
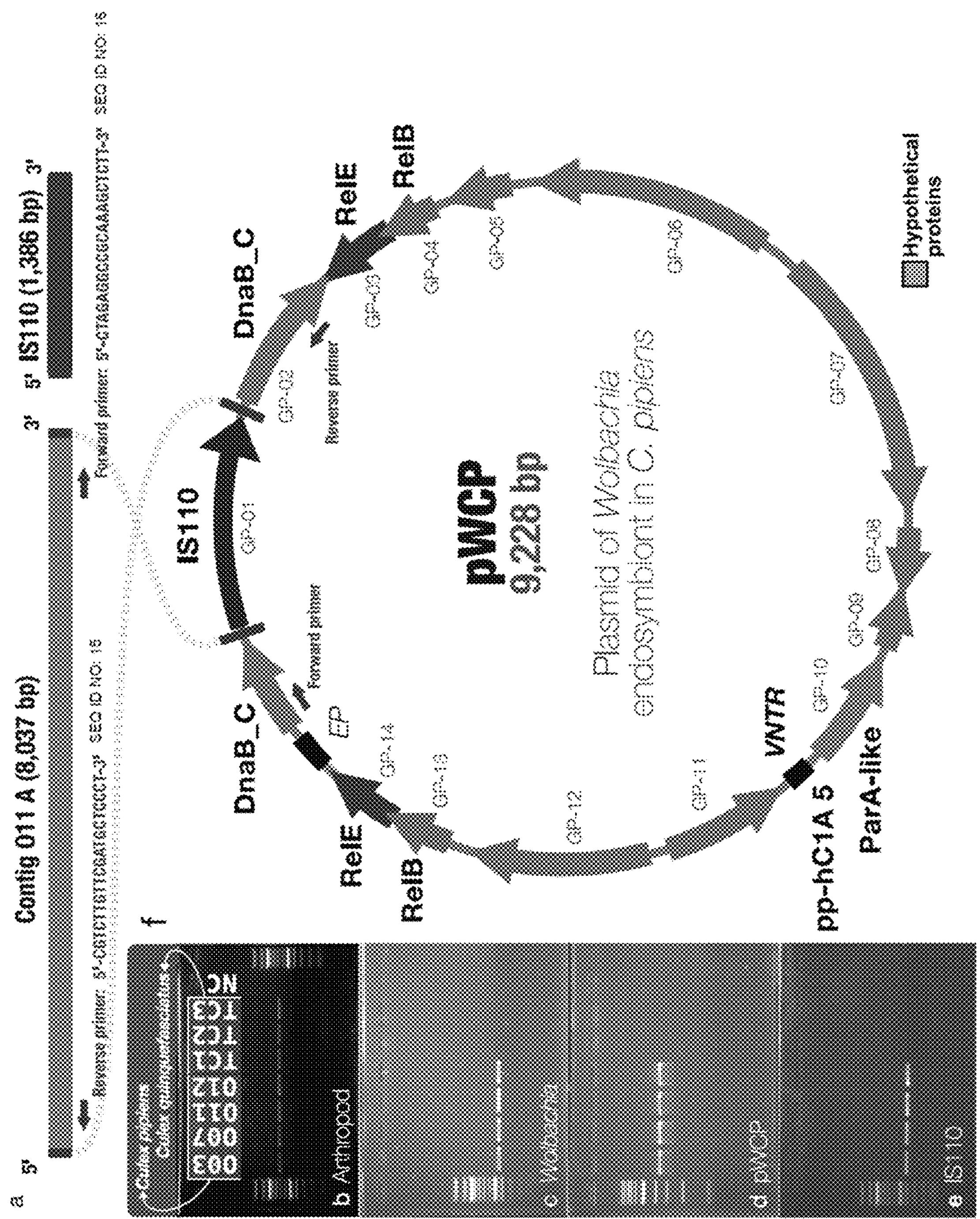
FIG. 1. The genome of the extrachromosomal element is circular. (a) illustrates Contig O11_A and IS110, respectively, identified in the assembly. The red ovals are regions of 100% nucleotide identity between the two contigs. Outward PCR primers were designed to amplify and confirm circularity of the sequence. (b, c, d, c) gels for PCR tests to confirm a *Wolbachia*-associated circular genome. To verify the presence of arthropod DNA in the four *Culex pipiens* studied herein and Tetracycline (TC) *Culex quinquefasciatus* treated samples a ca. 708 bp was PCR amplified using LCO1490 and HCO2198 primers (b). A ca. 438 bp fragment of the *Wolbachia* 16S rDNA gene (c), a ca. 1800 bp sequence amplified from outward primers illustrated in (a) that represents circularity of the genome (d) and a 431 bp of IS110 transposase (c) were obtained in wild *Culex pipiens* samples O03-O07-O11-O12 while no amplification was observed in *Wolbachia*-free samples. NC corresponds to Negative Control. (f) represents the complete genome. Each arrow represents an open reading frame (ORF). Open reading frames with no homology to a known function are shown in gray. ParA-like (green), RelBE toxin-antitoxin operon (blue), DnaB_C replicative DNA helicase (orange) which is disrupted by the ISWpi12 transposase of the IS110 family (purple) are represented by arrows (with an E-value$<e^{-12}$ from an NCBI Conserved Domain or Pfam Search). Black squares represent the location of (i) the variable number tandem repeat (VNTR), and (ii) the extragenic palindrome region (EP). 1 (a) Reverse primer: 5'-CGTCTTGTTCGATGCTCCCT-3' (SEQ ID NO: 15); 1 (b) Forward primer: 5'-CTAGAGGCCGCAAAGCTCTT-3' (SEQ ID NO: 16).

Disclosed herein are compositions, plasmids, and systems for use in methods of transforming *Wolbachia*. The inventors have identified, for the first time, an extrachromosomal plasmid within *Wolbachia*. Thus, the plasmids disclosed herein provide a method for the transformation of a *Wolbachia* cell, an organism that has been refractory to genetic manipulation techniques commonly used in other model organisms.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

The following definitions are provided for the full understanding of terms used in this specification.

Terminology

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.,* 22:1859-1862 (1981), or by the triester method according to Matteucci, et al., *J. Am. Chem. Soc.,* 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The term "polynucleotide" refers to a single or double stranded polymer composed of nucleotide monomers. In some embodiments, the polynucleotide is composed of nucleotide monomers of generally greater than 100 nucleotides in length and up to about 8,000 or more nucleotides in length.

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "target" refers to a molecule that has an affinity for a given probe. Targets may be naturally-occurring or man-made molecules. Also, they can be employed in their unaltered state or as aggregates with other species.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein.

A polynucleotide sequence is "heterologous" to a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from naturally occurring allelic variants.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" or "expression vector" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The term "plasmid" as used herein is commonly related to circular expression constructs comprising a covalenty closed circular DNA double-strand. Plasmids usually contain further sequences in addition to the ones, which should be expressed, like marker genes for their specific selection and in some cases sequences for their episomal replication in a cell.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism. For example, the sequence of a heterologous gene expressed in *Wolbachia* may be "codon optimized" to optimize gene expression based on the preferred codon usage in *Wolbachia*.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

"Transformation" refers to the transfer of a nucleic acid molecule into a host organism (e.g. *Wolbachia* cell). In embodiments, the nucleic acid molecule may be a plasmid that replicates autonomously or it may integrate into the genome of the host organism. Host organisms containing the transformed nucleic acid molecule may be referred to as "transgenic" or "recombinant" or "transformed" organisms. A "genetically modified" organism (e.g. genetically modified *Wolbachia*) is an organism that includes a nucleic acid that has been modified by human intervention. Examples of a nucleic acid that has been modified by human intervention include, but are not limited to, insertions, deletions, mutations, expression nucleic acid constructs (e.g. over-expression or expression from a non-natural promoter or control sequence or an operably linked promoter and gene nucleic acid distinct from a naturally occurring promoter and gene nucleic acid in an organism), extra-chromosomal nucleic acids, and genomically contained modified nucleic acids.

The term "fragment thereof" may refer to any portion of the given amino-acid sequence. Fragments may comprise more than one portion from within the full-length protein, joined together. Fragments may include small regions from the protein, or combinations of these.

The term "variant" or "derivative" as used herein refers to an amino acid sequence derived from the amino acid sequence of the parent protein having one or more amino acid substitutions, insertions, and/or deletions. It is understood that one way to define any known variants and derivatives or those that might arise, of the disclosed genes and proteins herein is through defining the variants and derivatives in terms of homology to specific known sequences. Specifically disclosed are variants of these and other genes and proteins herein disclosed which have at least, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes.

Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions can be made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the polypeptides provided herein.

As this specification discusses various proteins and protein sequences, it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Likewise, for nucleic acid sequences disclosed herein, it is understood that the proteins encoded by these sequences are also disclosed.

Plasmids and Methods of Use

Disclosed herein are plasmids and systems for use in methods of transforming *Wolbachia. The inventors have identified, for the first time, extrachromosomal plasmids within Wolbachia*. Thus, the plasmids disclosed herein provide a method for the transformation of a *Wolbachia* cell, an organism that has been refractory to genetic manipulation techniques commonly used in other model organisms.

In some aspects, disclosed herein is a non-naturally occurring plasmid comprising a first nucleic acid sequence capable of transforming a *Wolbachia* cell. In some embodiments, the plasmid further comprises a second nucleic acid sequence, wherein the second nucleic acid sequence is a heterologous nucleic acid sequence.

In one embodiment, the second nucleic acid sequence further comprises a heterologous gene. For example, the heterologous gene may be a gene from an arthropod. In one embodiment, the heterologous gene can include a reproductive parasitism gene to spread *Wolbachia* and/or its native anti-pathogen effects into hosts. In one embodiment, the heterologous gene can include a sterility or inviability gene that sterilizes or kills arthropod pests or vectors of disease. In one embodiment, the heterologous gene can include anti-pathogen genes, such as host immunity genes or those in the Octomom region of *Wolbachia* (WD0507-WD0514), that may protect insect hosts from viral infections. Examples of heterologous genes are found, for example, in WO2017/181043 and WO2017/214476.

In some embodiments, the first nucleic acid sequence comprises a gene encoding a transposase. In some embodiments, the transposase is selected from a member of the IS110 transposase family. In some embodiments, the transposase is selected from a member of the ISWpi12 group of transposases. In some embodiments, the transposase is encoded by SEQ ID NO: 1. In some embodiments, the transposase is encoded by a sequence at least 60% (for example, at least 60%, at least 65%, at least 70%, at least 75%, at least 80%, at least 85%, at least 90%, at least 95%) identical to SEQ ID NO:1, or a fragment or variant thereof.

In some embodiments, the transposase comprises SEQ ID NO:2. In some embodiments, the transposase is at least 60% (for example, at least 60%, at least 65%, at least 70%, at least 75%, at least 80%, at least 85%, at least 90%, at least 95%) identical to SEQ ID NO:2, or a fragment or variant thereof.

In some embodiments, the transposase is selected from Table 1. In some embodiments, the transposase is selected from *Wolbachia* IS110 family representatives including ISWen2, ISWpi13, or ISWpi14. In some embodiments, the transposase is selected from a non-*Wolbachia* bacteria, for example, *Listeria, Rickettsia*, or *Francisella*.

TABLE 1

*Wolbachia* IS110/ISWpi12 homologs

| Accession number | Genome | Locus tag(s) |
|---|---|---|
| WP_007302573.1 | wPip (Pel/JHB/Mol) | WP0440; WP1209; WP1347; C1A_1329; C1A_1307; C1A_762; C1A_1078; C1A_1101; WPM_01139 |
| WP_007303019.1 | wPip JHB | C1A_RS06995 |
| WP_015588780.1 | wHa | wHa_00350 |
| WP_017532054.1 | wDia | WDIAC_RS0102640 |
| WP_077190439.1 | wUni | N500_0696 |
| WP_017531734.1 | wDia | WDIAC_RS0100730 |
| WP_017532282.1 | wDia | WDIAC_RS0104035 |
| WP_082246113.1 | wVitA | N499_0602 |
| WP_017531969.1 | wDia | WDIAC_RS0102155 |
| WP_063630491.1 | wStr | WSTR_00305 |
| WP_063631169.1 | wStr | WSTR_05105 |
| BAH22240.1 | wCauB | B2gp35 |
| WP_017532059.1 | wDia | WDIAC_RS0102660 |
| ONI57730.1 | wVitA | N499_0602 |
| BAD16804.1 | wCauB | gp20 |
| WP_064085827.1 | wDacB | TV41_02665 |
| WP_108783963.1 | wBt1 | BQ3596_RS00370 |
| Pseudogene | wRi | WRi_p08700 |
| Pseudogene | wRi | WRi_p00380 |

In some embodiments, the first nucleic acid sequence comprises a ParA-like gene. In some embodiments, the ParA-like gene comprises SEQ ID NO:4. In some embodiments, the ParA-like gene is at least 60% (for example, at least 60%, at least 65%, at least 70%, at least 75%, at least 80%, at least 85%, at least 90%, at least 95%) identical to SEQ ID NO:4, or a fragment or variant thereof.

In some embodiments, the first nucleic acid sequence comprises a RelBE toxin-antitoxin operon. In some embodiments, the RelBE toxin-antitoxin operon comprises SEQ ID NO:5 or SEQ ID NO: 6. In some embodiments, the RelBE toxin-antitoxin operon is at least 60% (for example, at least 60%, at least 65%, at least 70%, at least 75%, at least 80%, at least 85%, at least 90%, at least 95%) identical to SEQ ID NO:5 (or a fragment or variant thereof) or SEQ ID NO:6 (or a fragment or variant thereof).

In some embodiments, the plasmid comprises one RelBE toxin-antitoxin operon. In some embodiments, the plasmid comprises two (or more) RelBE toxin-antitoxin operons. In some embodiments, the RelBE toxin-antitoxin operon comprises SEQ ID NO:5 or SEQ ID NO:6. In some embodiments, the RelBE toxin-antitoxin operon comprises SEQ ID NO:5. In some embodiments, the RelBE toxin-antitoxin operon comprises SEQ ID NO:6. In some embodiments, the RelBE toxin-antitoxin operon comprises SEQ ID NO:5 and SEQ ID NO:6.

In some embodiments, the plasmid further comprises a selectable marker. In some embodiments, the selectable marker comprises an antibiotic resistance marker. In some embodiments, the selectable marker comprises a tetracycline resistance marker. In some embodiments, the selectable marker comprises a fluorescent protein marker. In some embodiments, the selectable marker comprises a green fluorescent protein (GFP) marker.

In some embodiments, the heterologous nucleic acid sequence comprises a heterologous gene. In some embodiments, the heterologous gene is operably linked to a promoter active in the *Wolbachia* cell. In some embodiments, the promoter is a *Wolbachia* surface protein (wsp) promoter. In some embodiments, the plasmid is an isolated plasmid or purified plasmid.

In some embodiments, the plasmid comprises SEQ ID NO:3. In some embodiments, the plasmid is at least 60% (for example, at least 60%, at least 65%, at least 70%, at least 75%, at least 80%, at least 85%, at least 90%, at least 95%) identical to SEQ ID NO:3, or a fragment or variant thereof.

In some aspects, disclosed herein is a non-naturally occurring *Wolbachia* cell comprising one or more of the plasmids disclosed herein. In some embodiments, the cell is an isolated cell or a purified cell.

In some aspects, disclosed herein is a method for transforming a *Wolbachia* cell, comprising introducing a non-naturally occurring plasmid into the cell, wherein the plasmid comprises a first nucleic acid sequence capable of transforming a *Wolbachia* cell. In some embodiments, the plasmid further comprises a second nucleic acid sequence, wherein the second nucleic acid sequence is a heterologous nucleic acid sequence.

In one embodiment, the second nucleic acid sequence further comprises a heterologous gene. For example, the heterologous gene may be a gene from an arthropod. In one embodiment, the heterologous gene can include a reproductive parasitism gene to spread *Wolbachia* and/or its native anti-pathogen effects into hosts. In one embodiment, the heterologous gene can include a sterility or inviability gene that sterilizes or kills arthropod pests or vectors of disease. In one embodiment, the heterologous gene can include anti-pathogen genes, such as host immunity genes or those in the Octomom region of *Wolbachia* (WD0507-WD0514), that have been shown to protect insect hosts from viral infections. Examples of heterologous genes are found, for example, in WO2017/181043 and WO2017/214476.

In some embodiments, the first nucleic acid sequence comprises a gene encoding a transposase. In some embodiments, the transposase is selected from a member of the IS110 transposase family. In some embodiments, the transposase is selected from a member of the ISWpi12 group of transposases. In some embodiments, the transposase is encoded by SEQ ID NO: 1. In some embodiments, the transposase is encoded by a sequence at least 60% (for example, at least 60%, at least 65%, at least 70%, at least 75%, at least 80%, at least 85%, at least 90%, at least 95%) identical to SEQ ID NO:1, or a fragment or variant thereof.

In some embodiments, the transposase comprises SEQ ID NO:2. In some embodiments, the transposase is at least 60% (for example, at least 60%, at least 65%, at least 70%, at least 75%, at least 80%, at least 85%, at least 90%, at least 95%) identical to SEQ ID NO:2, or a fragment or variant thereof.

In some embodiments, the transposase is selected from Table 1. In some embodiments, the transposase is selected from *Wolbachia* IS110 family representatives including ISWen2, ISWpi13, or ISWpi14. In some embodiments, the transposase is selected from a non-*Wolbachia* bacteria, for example, *Listeria, Rickettsia*, or *Francisella.*

In some embodiments, the first nucleic acid sequence comprises a ParA-like gene. In some embodiments, the ParA-like gene comprises SEQ ID NO:4. In some embodiments, the ParA-like gene is at least 60% (for example, at least 60%, at least 65%, at least 70%, at least 75%, at least 80%, at least 85%, at least 90%, at least 95%) identical to SEQ ID NO:4, or a fragment or variant thereof.

In some embodiments, the first nucleic acid sequence comprises a RelBE toxin-antitoxin operon. In some embodiments, the RelBE toxin-antitoxin operon comprises SEQ ID NO:5 or SEQ ID NO: 6. In some embodiments, the RelBE toxin-antitoxin operon is at least 60% (for example, at least 60%, at least 65%, at least 70%, at least 75%, at least 80%, at least 85%, at least 90%, at least 95%) identical to SEQ ID NO:5 (or a fragment or variant thereof) or SEQ ID NO:6 (or a fragment or variant thereof).

In some embodiments, the plasmid comprises one RelBE toxin-antitoxin operon. In some embodiments, the plasmid comprises two (or more) RelBE toxin-antitoxin operons. In some embodiments, the RelBE toxin-antitoxin operon comprises SEQ ID NO:5 or SEQ ID NO:6. In some embodiments, the RelBE toxin-antitoxin operon comprises SEQ ID NO:5. In some embodiments, the RelBE toxin-antitoxin operon comprises SEQ ID NO:6. In some embodiments, the RelBE toxin-antitoxin operon comprises SEQ ID NO:5 and SEQ ID NO:6.

In some embodiments, the plasmid further comprises a selectable marker. In some embodiments, the selectable marker comprises an antibiotic resistance marker. In some embodiments, the selectable marker comprises a tetracycline resistance marker. In some embodiments, the selectable marker comprises a fluorescent protein marker. In some embodiments, the selectable marker comprises a green fluorescent protein (GFP) marker.

In some embodiments, the heterologous nucleic acid sequence comprises a heterologous gene. In some embodiments, the heterologous gene is operably linked to a promoter active in the *Wolbachia* cell. In some embodiments, the promoter is a *Wolbachia* surface protein (wsp) promoter.

In some embodiments, the plasmid comprises SEQ ID NO:3. In some embodiments, the plasmid is at least 60% (for example, at least 60%, at least 65%, at least 70%, at least 75%, at least 80%, at least 85%, at least 90%, at least 95%) identical to SEQ ID NO:3, or a fragment or variant thereof.

In some aspects, disclosed herein is a *Wolbachia* transformation system comprising a first nucleic acid sequence capable of transforming a *Wolbachia* cell and a second nucleic acid sequence, wherein the second nucleic acid sequence is a heterologous nucleic acid sequence.

In one embodiment, the system further comprises dendrimers. In one embodiment, the system further comprises complex G4 dendrimers.

In another aspect, disclosed herein is a *Wolbachia* cell, wherein said *Wolbachia* cell is a symbiont of an insect, wherein the *Wolbachia* cell is transformed with a plasmid herein to express a heterologous gene, wherein the expression of the heterologous gene decreases the ability of the insect to transmit a pathogen.

In another aspect, disclosed herein is a *Wolbachia* cell, wherein said *Wolbachia* cell is a symbiont of an insect, wherein the *Wolbachia* cell is transformed with a plasmid herein to express a heterologous gene, wherein the expression of the heterologous gene decreases the reproductive potential of the insect.

In another aspect, disclosed herein is a *Wolbachia* cell, wherein said *Wolbachia* cell is a symbiont of an insect, wherein the *Wolbachia* cell is transformed with a plasmid herein to express a heterologous gene, wherein the expression of the heterologous gene sterilizes the insect.

In another aspect, provided herein is a *Wolbachia* cell wherein said *Wolbachia* cell is a symbiont of an insect, wherein the *Wolbachia* cell is transformed with a plasmid herein to express an RNA (a single stranded RNA or a double stranded RNA), wherein the RNA decreases the expression of at least one selected target gene of the insect.

In one embodiment, the insect is an arthropod. In one embodiment, the arthropod is a mosquito. In one embodiment, the mosquito is selected from the genera consisting of *Aedes, Culex* and *Anopheles*. In one embodiment, the mosquito is an *Aedes* mosquito. In one embodiment, the mosquito is an *Anopheles* mosquito. In one embodiment, the mosquito is a *Culex* mosquito. In one embodiment, the *Aedes* mosquito species is selected from the group consisting of *Aedes albopictus, Aedes aegypti* and *Aedes polynesiensis*. In one embodiment, the *Anopheles* mosquito species is *Anopheles gambiae*. In one embodiment, the *Culex* mosquito species is *Culex pipiens*. In one embodiment, the insect is *Drosophila* suzukii.

In one embodiment, the pathogen is selected from dengue virus, Zika virus, a malaria parasite (*Plasmodium* genus), West Nile virus, yellow fever virus, chikungunya virus, Japanese encephalitis, St. Louis encephalitis and Western and Eastern Equine Encephalitis viruses.

In one aspect, provided herein is a method for treating a filarial nematode infection in a host, comprising the steps: administering a plasmid described herein to the host, wherein delivery of the plasmid into a *Wolbachia* cell causes lysis or inhibits the growth of the *Wolbachia* cell.

In one embodiment, the administration of the plasmid to a host causes lysis of the *Wolbachia* cell. In one embodiment, the administration of the plasmid to a host inhibits the growth of the *Wolbachia* cell.

In one embodiment, the heterologous gene is operably linked to a promoter active in the host cell. In one embodiment, the vector further comprises a selectable marker. The selectable marker can be, for example, a tetracycline resistance marker or green fluorescent protein (GFP) marker.

In one embodiment, the filarial infection is *Onchocerca volvulus* (river blindness). In one embodiment, the filarial infection is selected from *Wuchereria bancrofti, Brugia malayi* or *B. timori*. (lymphatic filariasis). In one embodiment, the filarial infection is *Dirofilaria immitis* (canine heartworm). In some embodiments, the plasmid can be used to treat veterinary diseases due to infection with filarial worms.

EXAMPLES

The following examples are set forth below to illustrate the compositions, systems, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. The *Wolbachia* Mobilome in *Culex pipiens* Includes a Plasmid

*Wolbachia* are a widespread genus of obligate intracellular bacteria that occur in arthropod and nematode species worldwide. The bacteria were first described in detail in the gonads of the mosquito *Culex pipiens* nearly a century ago, and later demonstrated in the same host to be the causative agent of cytoplasmic incompatibility (CI), a microbial drive system at the foreground of vector control efforts. CI is meditated by temperate bacteriophage WO that was also first observed in *Culex pipiens*, putting mobile genetic elements at the forefront of *Wolbachia* genomic studies.

In the example herein, shotgun metagenomes were generated and analyzed from the ovaries of four individual wild *Culex pipiens* captured in Southern France. Using state-of-the-art assembly and binning strategies, near-complete *Wolbachia* genomes were reconstructed from each individual, and in addition to novel viral genes missing from the *Wolbachia* reference genome, it is reported herein the discovery of the first plasmid for this genus. The plasmid 'pWCP' for Plasmid of *Wolbachia* endosymbiont in *C. pipiens* is a 9.23 kbp circular element with 14 genes, and it is estimated that it occurs on average in four to six copies per *Wolbachia* cell. The presence of the pWCP in additional *Culex* samples was further validated. The example herein provides for new plasmids and systems based on the identification of a previously unrecognized extrachromosomal element of *Wolbachia* and provides methods for genetic manipulation of this fastidious and widespread bacteria.

BACKGROUND

Mosquitoes are major vectors of disease-causing pathogens worldwide including viruses such as dengue, West Nile, Chikungunya, Zika, and yellow fever (Boyer et al. 2018; Gould et al. 2017; Shragai et al. 2017). In the absence of effective vaccines and mosquito control strategies concomitant to a deleterious use of insecticides, novel vector biocontrol efforts are the focus of current study (Flores and O'Neill 2018). Over the last decade, the widely distributed endosymbiotic alpha-proteobacteria *Wolbachia* in arthropods has gained attention not only as a reproductive parasite that spreads itself at the expense of host fitness, but also as a new tool to control the transmission of diseases due to its capacity to block virus transmission and to manipulate host reproduction (Ant et al. 2018; Joubert et al. 2016; Joubert and O'Neill 2017). Native *Wolbachia* reduce viral replication in the fruit fly *Drosophila* (Hedges et al. 2008; Jeffries and Walker 2016; Teixeira, Ferreira, and Ashburner 2008), and *Wolbachia* transinfections in mosquito species (i.e., *Aedes aegypti*, Ae. *albopictus*, Ae. *polynesienses* and *Anopheles stephensi*) result in pathogen-refractory mosquito lines (Andrews et al. 2012; Bian et al. 2013; Blagrove et al. 2012; Joubert and O'Neill 2017; McMeniman et al. 2009).

*Wolbachia* is transovarially transmitted from the mother to offspring (Ferree et al. 2005; Funkhouser-Jones et al. 2018; LePage and Bordenstein 2013; Serbus and Sullivan 2007). In some arthropods, *Wolbachia* 'modifies' sperm in testes, which leads to embryonic lethality if the infected male mates with an uninfected female. When both male and female are infected with the same *Wolbachia* strain, the modification is 'rescued', and the compatibility is restored (Werren 1997). However, if the male and female are infected by *Wolbachia* populations with different 'modification-rescue' systems, it results in a bi-directional incompatibility (Atyame et al. 2014; Laven 1967). This alteration, termed 'cytoplasmic incompatibility' (CI), is the most common *Wolbachia*-induced reproductive manipulation and can lead to population replacement by *Wolbachia*-infected strains. The 'Two-by-One' model describes the genetic basis of CI whereby two genes, cytoplasmic incompatibility factors cifA and cifB (Beckmann, Ronau, and Hochstrasser 2017; LePage et al. 2017; Shropshire et al. 2018) are required to induce CI, and one of the same genes, cifA, rescues CI in the fertilized embryo (Shropshire et al. 2018). These genes are located in the eukaryotic association module of *Wolbachia*'s phage WO (Bordenstein and Bordenstein 2016; LePage et al. 2017; Shropshire et al. 2018) that exhibits a temperate lifecycle, laterally transfers between *Wolbachia* coinfections, and evolves rapidly with frequent insertion/deletion events (Bordenstein and Wernegreen 2004; Chafee et al. 2010; Kent, Funkhouser, et al. 2011; Kent, Salichos, et al. 2011). Phage WO genes underpin *Wolbachia*'s ability to hijack sperm and egg via CI (LePage et al. 2017), and variation in these genes may account for phenotypic variation in CI within various insects species (Bonneau et al. 2018; LePage et al. 2017). These recent observations emphasize the importance of investigating genetic structures beyond the *Wolbachia* bacterial chromosome to study the complex interplay between arthropods and their endosymbionts.

While recent studies shed light on phage WO's roles in *Wolbachia* genome evolution and CI, other extrachromosomal elements, such as plasmids, have not been detected in *Wolbachia*. Notably, over half of the species in the closely-related *Rickettsia* genus have plasmids (El Karkouri et al. 2016) that play roles in DNA replication, partitioning, mobilization, and conjugation (Baldridge et al. 2007; Ogata et al. 2005), and offer a potential tool for genetic manipulation of diverse members of *Rickettsia* (Burkhardt et al. 2011; Wood et al. 2012). Previous efforts to search for such extrachromosomal mobile genetic elements in *Wolbachia* have not been successful (Sun et al. 2001; Woolfit et al. 2013). The lack of isolates limit direct insights into *Wolbachia* genomics, and most metagenomic approaches thus far rely on pooled individuals grown in the lab environment due to low infection densities (Iturbe-Ormaetxe et al. 2011; Klasson et al. 2008). Since these limitations can conceal naturally occurring genomic diversity among *Wolbachia* populations, highly resolved analyses of individual mosquitoes may reveal additional insights into the *Wolbachia* 'mobilome', the pool of all mobile genetic elements associated with *Wolbachia* populations.

Here, ovary samples were sequenced from four wild-caught *Culex pipiens* individuals captured in Southern France from a single trap. Using genome-resolved metagenomic and pangenomic analysis strategies, near-complete *Wolbachia* genomes from each individual were reconstructed and compared. Besides a diverse set of phage-associated genes that were missing or absent in the reference *Wolbachia* genome wPip, this data reveals the first evidence for an extrachromosomal circular element with genetic and functional hallmarks of a plasmid that is referred to herein as pWCP.

Results

Shotgun sequencing of DNA recovered from ovary samples of four *Culex pipiens* individuals (O03, O07, O11, O12) resulted in 65 to 78 million paired-end sequences after quality filtering. Metagenomic assembly of each sample individually yielded 147K to 183K contiguous DNA segments (contigs) longer than 1 kbp, which recruited back 49.6% to 70.1% of the raw sequencing reads. A metagenomic binning strategy was employed that uses sequence composition signatures and differential coverage statistics of contigs across samples. For each ovary sample, a highly-complete single bacterial metagenome-assembled genome (MAG) was reconstructed that resolved to *Wolbachia* (Table 2).

TABLE 2

*Wolbachia* metagenome-assembled genome (MAGs) with completion and redundancy estimates, number of contigs (N), number of genes (n), total number of nucleotides and % GC. More than 90% completion and less than 10% redundancy based on the single occurrence of 139 single-copy genes (SCG) identified from the collection of (Campbell et al. 2013) suggest high completion of the bins.

| MAG | Percent completion (PC) | Percent redundancy (PR) | Number of contigs (N) | Number of genes (n) | Length (total number of nucleotides) | GC content (%) |
|---|---|---|---|---|---|---|
| O03 | 94.24 | 0.72 | 93 | 1091 | 1,213,072 | 33.83 |
| O07 | 94.24 | 0.72 | 127 | 1181 | 1,317,313 | 33.78 |
| O11 | 94.24 | 0 | 99 | 1085 | 1,208,099 | 33.84 |
| O12 | 94.24 | 0 | 99 | 1113 | 1,237,800 | 33.95 |

Figure 4:
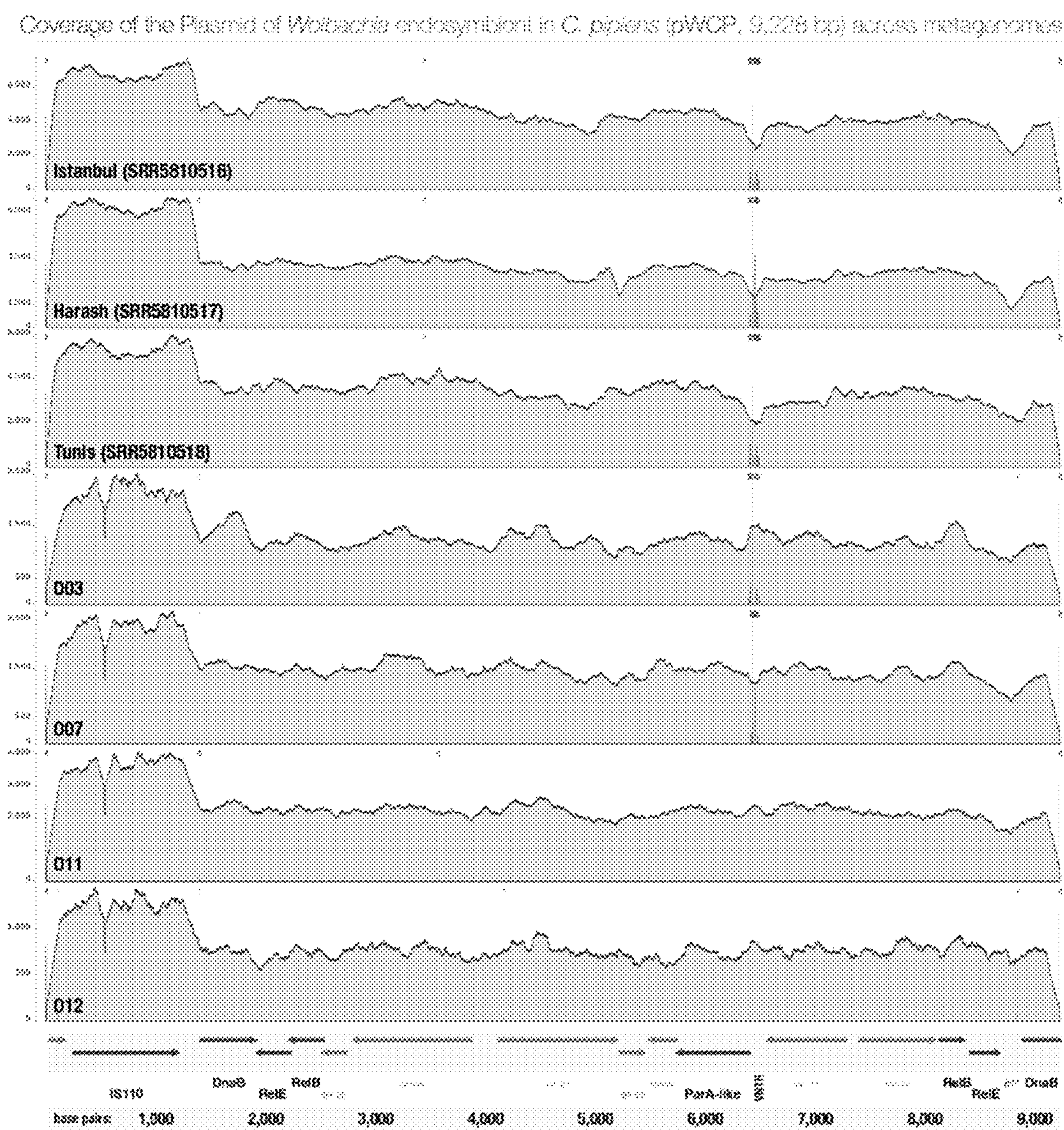
FIG. 4. Metagenomic read recruitment onto the circularized contig, referred to herein as 'pWCP' (for Plasmid of *Wolbachia* endosymbiont in *C. pipiens*), showed consistent coverage over its entire length except a clear two-fold coverage increase in a region that matched to the IS110 element in all four *Culex* individuals in this study.

*Wolbachia* Genomes Reconstructed from Individual *C. pipiens* Ovaries Show Differentially Covered Bacterial, Phage, as Well as Extrachromosomal Element Contigs The relatively low number of single-nucleotide variants suggested that each *Wolbachia* MAG represented a nearly-monoclonal population of bacterial cells in the ovary metagenomes. In addition, the high average nucleotide identity across the MAGs and the 1,482 kbp reference genome for *Wolbachia*, wPip (Klasson et al. 2008) (99.1% to 99.98%), suggested a high degree of conservation between the endosymbionts of different individuals. The metagenomic read recruitment analyses using *Wolbachia* MAGs revealed consistent coverage statistics averaging 168× to 311× for contigs that were enriched with bacterial genes. However, a subset of contigs displayed considerably higher coverage values that averaged 477× to 1,519×. Because *Wolbachia* harbor prophage WO that can enter the lytic cycle and form phage particles (Bordenstein and Bordenstein 2016; Sanogo and Dobson 2006; Wright et al. 1978), some of the contigs could be phage-associated, which would explain coverage inconsistencies. The five prophage regions identified in the wPip reference genome (Bordenstein and Bordenstein 2016; Klasson et al. 2008) were used to identify contigs enriched with genes of phage-origin. Contigs classified and validated through homology searches against 'phage WO' matched to contigs that were highly covered in the MAGs, confirming that most shifts in coverage could be attributed to phages of *Wolbachia*. However surprisingly, five contigs in the MAGs (Contig O12_A, Contig O11_A, Contig O07_A, Contig O07_A' and Contig O03_A) showed no homology to prophage WO despite their remarkable coverage which ranged between 720× to 2,176×. Interestingly, the 5' and 3' ends of these contigs showed homology to the non-coding flanking regions of wPip's ISWpi12 transposases (WP0440, WP1209, and WP1347) of the IS110-family. Given their (1) high coverage in metagenomes, (2) lack of homology to prophage WO, and (3) putative association with the IS110 transposase, it was hypothesized that these contigs could represent extrachromosomal elements.

pWCP: An Extrachromosomal Circular Element that Contains a Transposase, Occurs Together with *Wolbachia* and is Near-Identical Across Individual Mosquitoes Based on homology between the ends of these five contigs and the flanking regions of IS110, it was predicted that the missing region was the IS110 transposase. To investigate the presence of such an extrachromosomal circular element, Contig O11_A (8,037 bp) was circularized and an IS110 transposase sequence was inserted (1,386 bp) based on the overlapping 5' and 3' ends. Metagenomic read recruitment onto this artificially circularized contig, referred to herein as 'pWCP' (for Plasmid of *Wolbachia* endosymbiont in *C. pipiens*), showed consistent coverage over its entire length except a clear two-fold coverage increase in a region that matched to the IS110 element in all four *Culex* individuals in this study (FIG. 4). Read recruitment analyses onto the extrachromosomal element i) without any inserted IS element and ii) with another IS inserted (i.e, IS982) designed to detect a potential artefactual read mapping, showed a drastic decrease and increase of coverage, respectively (data not presented), further supporting the circularity of the molecule with an inserted IS110 transposase. The read recruitment from three metagenomes generated in a previous study by (Bonneau et al. 2018) using *Culex* eggs confirmed the near identical presence of pWCP in all three, along with the observed increase in coverage matching to IS110 gene (FIG. 4).

To further validate the presence of a circular replicon and its association with *Wolbachia*, primers were designed from the 5' (reverse) and 3' (forward) ends of Contig O11_A going outward with a predicted 2 kbp span (FIG. 1*a*, see Table 3 for primer sequences 263F and 2127R). In addition, primers were designed to Sanger sequence across the circular gap (see Table 3 for primer sequences EC_4F and EC_4R).

TABLE 3

Primers for detecting *Wolbachia* plasmid

| Primer name | Sequence |
|---|---|
| 263F | 5'-CTAGAGGCCGCAAAGCTCTT-3' (SEQ ID NO: 7) |
| 2127 R | 5'-CGTCTTGTTCGATGCTCCCT-3' (SEQ ID NO: 8) |
| EC_4F | 5'-ACACATCGAGCTAATACCCGT-3' (SEQ ID NO: 9) |
| EC_4R | 5' CCAAGCTCTGGCATTAAACAG A-3' (SEQ ID NO: 10) |

First, using LCO1490 and HCO2198 mitochondrial cytochrome c oxidase subunit I (COI) invertebrate primers (Folmer et al. 1994), the presence of a ~708 bp band was detected in the four *Culex pipiens* individuals and the three *Wolbachia*-free *Culex quinquefasciatus* controls treated with Tetracycline, confirming the presence of arthropod DNA in all samples (FIG. 1*b*). Next, the presence of *Wolbachia* DNA in the four first samples were verified by PCR amplifying a 438 bp fragment of the *Wolbachia* 16S rRNA gene using Wspec-F and Wspec-R primers (Werren and Windsor 2000) while no band was observed in the Tetracycline samples, confirming the infection status of *Wolbachia*-positive vs. *Wolbachia*-free samples (FIG. 1*c*). Critically, a ~1,800 bp fragment amplified with primers 263 F and 2,127 R (Table 3) designed from the ends of the artificially circularized contig within DnaB gene, confirmed the circular nature of the pWCP and its presence only in *Wolbachia*-infected *Culex* samples (FIG. 1*d*). Finally, the IS110 transposase was amplified with primers EC_4F and EC_4R (Table 3) in the four *Culex* samples studied herein while observing no band in the *Wolbachia*-free samples (FIG. 1*e*), confirming the presence of a circular chromosome with an IS associated to *Wolbachia* (FIG. 1*f*). These results were further confirmed using additional Rifampicin and Oxytetracycline treated *Culex pipiens* samples (data not shown).

The average nucleotide identity of the four pWCP sequences independently assembled from four individual mosquitoes was 99.65% to 100% (Table 4). In addition, a 8,315 bp contig was identified in the wPip JHB assembly (ABZA01000008.1; Salzberg 2009) which also was more than 99.53% identical to each of the four pWCP sequences (Table 4). The IS110 transposase was 100% identical across samples and confirmed as clonal. The additional read recruitment analyses from publicly available metagenomes (SAMN07327406, SAMN07327402, SAMN07315580, (Bonneau et al. 2018) also revealed the widespread occurrence of pWCP in *Culex* individuals from Turkey, Morocco, and Tunisia at a similar 4.2 to 7.3-fold higher copy number relative to the *Wolbachia* genome. It was also confirmed that pWCP and *Wolbachia* bacterial chromosome display a similar tetranucleotide composition. Overall, these findings suggest that pWCP is maintained with the *Wolbachia* main chromosome at each cell-division.

TABLE 4

| Comparison of pWCP sequences | | | | | |
|---|---|---|---|---|---|
| | Culex_JHB | Culex_O11 | Culex_O12 | Culex_003 | Culex_O07 |
| Culex_JHB | | 99.74% | 99.74% | 99.94% | 99.53% |
| Culex_O11 | 99.74% | | 100% | 99.79% | 99.81% |
| Culex_O12 | 99.74% | 100% | | 99.79% | 99.81% |
| Culex_003 | 99.94% | 99.79% | 99.79% | | 99.65% |
| Culex_O07 | 99.53% | 99.81% | 99.81% | 99.65% | |

pWCP Encodes an ISWpi12-IS110 Family Transposase, an Intergenic Variable Number Tandem Repeat (VNTR) Region, a ParA-Like Gene, a relBE Toxin-Antitoxin Locus, Disrupted DnaB and Several Hypothetical Proteins The IS transposase matched to the ISWpi12 of the IS110 family (Cerveau et al. 2011) based on a homology search using the IS finder platform. Besides the ISWpi12 transposase, functional annotation of genes in pWCP revealed the presence of a disrupted DnaB-like helicase, two RelBE loci, a ParA-like gene, and multiple hypothetical proteins (FIG. 1*f*, Table 5). ParA-like partitioning gene showed amino-acid homology to the chromosome partitioning of plasmids (ParA) identified in Ca. *Caedibacter acanthamoebae* (an endosymbiont of *acanthamoebae*; e-value: $2\times10^{-46}$), the bacterium *Odyssella thessalonicensis* (e-value: $9\times10^{-45}$), and *Rickettsia raoultii* (e-value: $7\times10^{-41}$). The RelBE toxin-antitoxin (TA) operon system has been identified in multiple *Wolbachia* genomes (Singhal and Mohanty 2018) and is often associated with prophage WO regions (e.g., of wVitA, wHa, wMel, wAu, wRi, wSuzi, wFol, wInc), specifically the tail and/or capsid modules. In other bacteria, this TA system can promote the stability of its encoding mobile element, such as plasmid or pathogenicity island, through post-segregational killing of cells that have lost the antitoxin component of the TA operon (Harms et al. 2018; Shao et al. 2011). Most remaining pWCP genes were hypothetical and unique to either wPip and/or B-*Wolbachia* phyletic super-group (Lo et al. 2002, Table 5), including GP-08 and GP-09 which showed a very weak homology to a Transcription Factor and a Terminase, respectively (e-value>0 in SCOPe, Pfam and COG). In particular, terminase proteins bind and package DNA into the phage capsid (Shen et al. 2012). These data could indicate the extrachromosomal DNA could fall into three categories, that is a simple plasmid, a mini-chromosome of *Wolbachia*, or a plasmid-like replicon that hijacks the capsids of phage WO.

TABLE 5

| pWCP loci | | |
|---|---|---|
| Locus tag | NCBI Conserved Domain | Evalue |
| GP-01 | IS110 Transposase | 4.02E−19 |
| GP-02 C terminal | Replicative DnaB-like helicase C terminal domain | 1.60E−68 |
| GP-02 N terminal | Replicative DnaB-like helicase N terminal domain | 1.90E−29 |
| GP-03 | RelE | 1.76E−13 |
| GG-10 | ParA-like | 7.53E−26 |
| GP-14 | RelE | 4.08E−13 |

Figure 2:
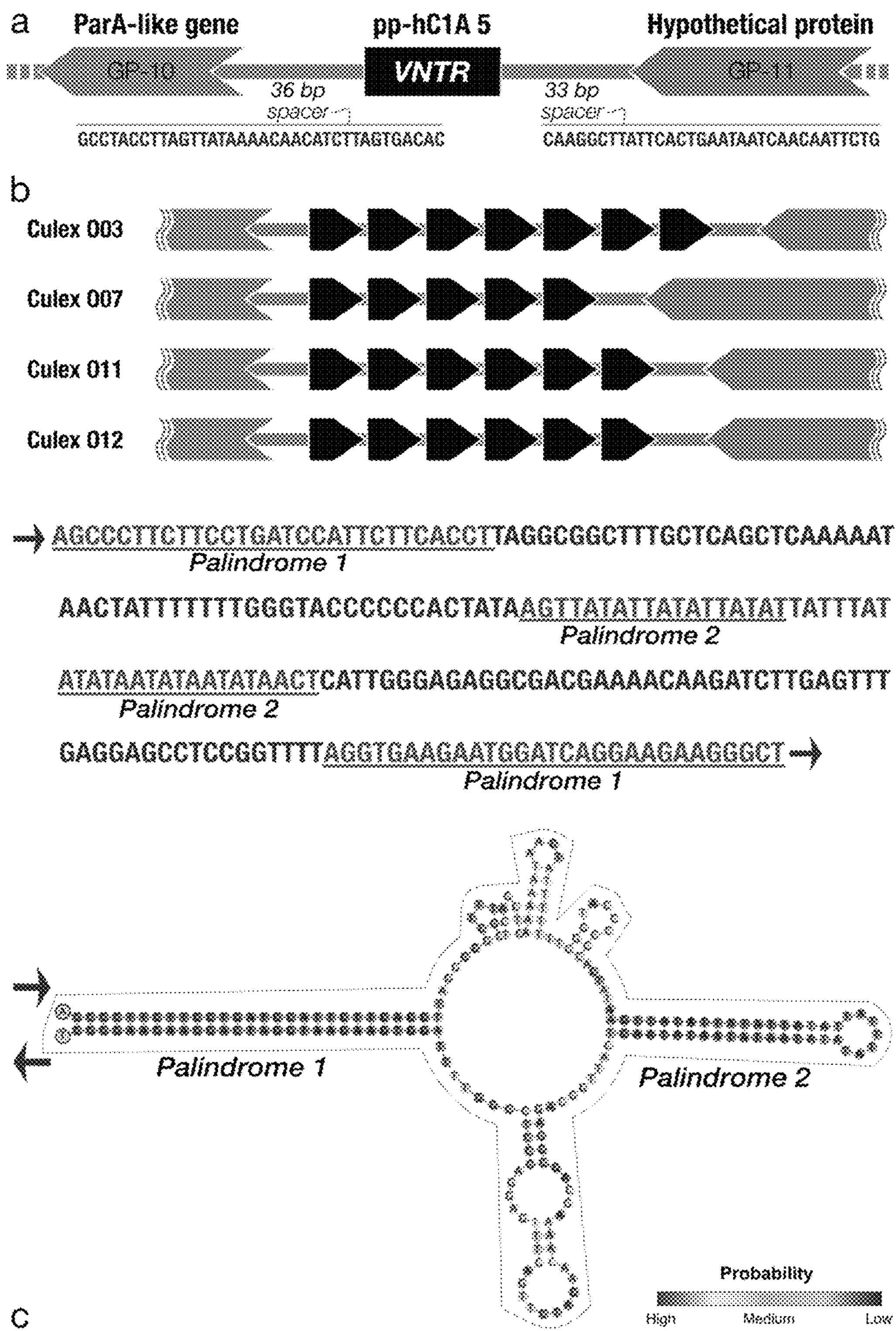
FIG. 2. pWCP contains a VNTR region and extragenic palindrome sequence. (a) A VNTR region is located between parA and a hypothetical protein in the circular genome. While the number of repeats varies across individuals (b), the 36- and 33-bp spacers are conserved. Each black arrow represents a 16-nt repeat. The predicted DNA structure of the extragenic palindrome sequence is illustrated in (c) where color indicates probability of each base pairing. Red represents the strongest probability while blue is the lowest. 2 (a) GCCTACCTTAGTTATAAAACAACATCTTAGTGACAC (SEQ ID NO: 17) and CAAGGCTTATTCACTGAATAATCAACAATTCTG (SEQ ID NO: 18). 2 (c) AGCCCTTCTTCCTGATCCATTCTTCACCTTAGGCGGCTTTGCTCAGCTCAAAAATAAC TATTTTTTTGGGTACCCCCCACTATAAGTTATATTATATTATATTATTTATATATAATA TAATATAACTCATTGGGAGAGGCGACGAAAACAAGATCTTGAGTTTGAGGAGCCTC CGGTTTTAGGTGAAGAATGGATCAGGAAGAAGGGCT (SEQ ID NO: 19).

Beyond the putative coding regions, alignment of all contigs revealed a VNTR region (FIGS. 2*a* and 2*b*), characterized as 16-nt repeats adjacent to parA that vary in number among individual pWCP sequences. Recent studies observed the same repeat region, identified as pp-hClA_5, and used it to genotype different strains of *Wolbachia* in *Culex* (Petridis and Chatzidimitriou 2011; Riegler et al. 2012), yet these have not been studied at an individual level. The authors suggested that a deletion in the intergenic polymorphic region could serve as a recombination or horizontal gene transfer site (Petridis and Chatzidimitriou 2011). Alternatively, the direct repeats, as present in iteron plasmids, could indicate a potential origin of replication and play a role in copy number control (Konieczny et al. 2014). This analysis of the pWCP sequence also revealed a 209 bp extragenic palindrome (EP) region with two palindromes (FIG. 2*c*). Although the role of these sequences is not clear, the plasmid of *Rickettsia monacensis* (pRM) harbors four perfect and four imperfect palindromes (Baldridge et al. 2007).

The *Wolbachia* Pangenome Reveals a Diverse Set of Individual-Specific Phage Genes that are Missing from the wPip Reference Genome The assembly and binning of individual mosquitoes from the wild also allowed characterization of the diversity and the gene content of prophage regions in these *Wolbachia* genomes in comparison to the wPip reference genome. For this, a metapangenomic analysis was performed of the four *Wolbachia* MAGs and wPip in conjunction with the four metagenomes from individual mosquitoes to link phylogenetic relationships between genes and their abundances in *C. pipiens* metagenomes. To recover gene coverages, the *Wolbachia* MAG 007 was used as reference for read recruitment since (1) it was the largest MAG in size with most number of genes (Table 2), and (2) all MAGs were over 99.8% identical.

The *Wolbachia* pangenome contained 1,166 gene clusters (that is, groups of homologous predicted open reading frames based on amino acid sequence identity), the majority of which were conserved across all five genomes (FIG. 3, FIG. 5), wPip and *Wolbachia* MAG 007 carried the largest number of unique gene clusters. Accessory genes that were unique to wPip (n=41) encoded functions including several transposases, bacteriophage capsid protein coding genes, and other phage-related sequences, most of which were associated with known *Wolbachia* prophages. Gene clusters unique to MAG 007 (n=56) included a gene coding for an ankyrin and tetratricopeptide repeats previously identified in phage WO from *Nasonia vitripennis* wasps (Bordenstein and Bordenstein 2016). Ankyrin and tetratricopeptide repeats mediate a broad range of protein-protein interactions (apoptosis, cell signaling, inflammatory response, etc.) within eukaryotic cells and are commonly associated with effector proteins of certain intracellular pathogens (Cerveny et al. 2013; Pan et al. 2008). There is also Retron-type reverse transcriptase, and genes coding for Transposases (COG3293 and a Transposase InsO and inactivated derivatives gene. Although most remaining unique 007 gene clusters had no functional annotation, about a third matched to eukaryotic viral genes based on homology searches in the NCBI's non-redundant protein sequence database (data not shown).

These data add to previous studies showing that regions of genomic diversity between closely related *Wolbachia* genomes are often virus-associated (Ishmael et al. 2009; Klasson et al. 2009; Salzberg et al. 2009; Siozios et al. 2013). Note that most gene clusters with genes that were unique to MAG 007 did recruit reads from the three other metagenomes (FIG. 3, FIG. 5), suggesting that even though they were not characterized in the MAGs, they did occur in *Culex* metagenomes. Absence of these genes from the MAGs are most likely due to (1) assembly artifacts that result in fragmented contigs that are too short to be considered for binning, or (2) mutations in the gene context that affect the gene caller to identify them properly. Gene clusters that matched to pWCP were also among those that occurred only among *Wolbachia* MAGs, and missing in wPip (FIG. 5) (Klasson et al. 2008). Overall, the metapangenome sheds light on a substantial amount of viral genetic diversity, revealing almost as many virus-associated genes as the ones that were previously recognized in the reference genome wPip.

Figure 3:
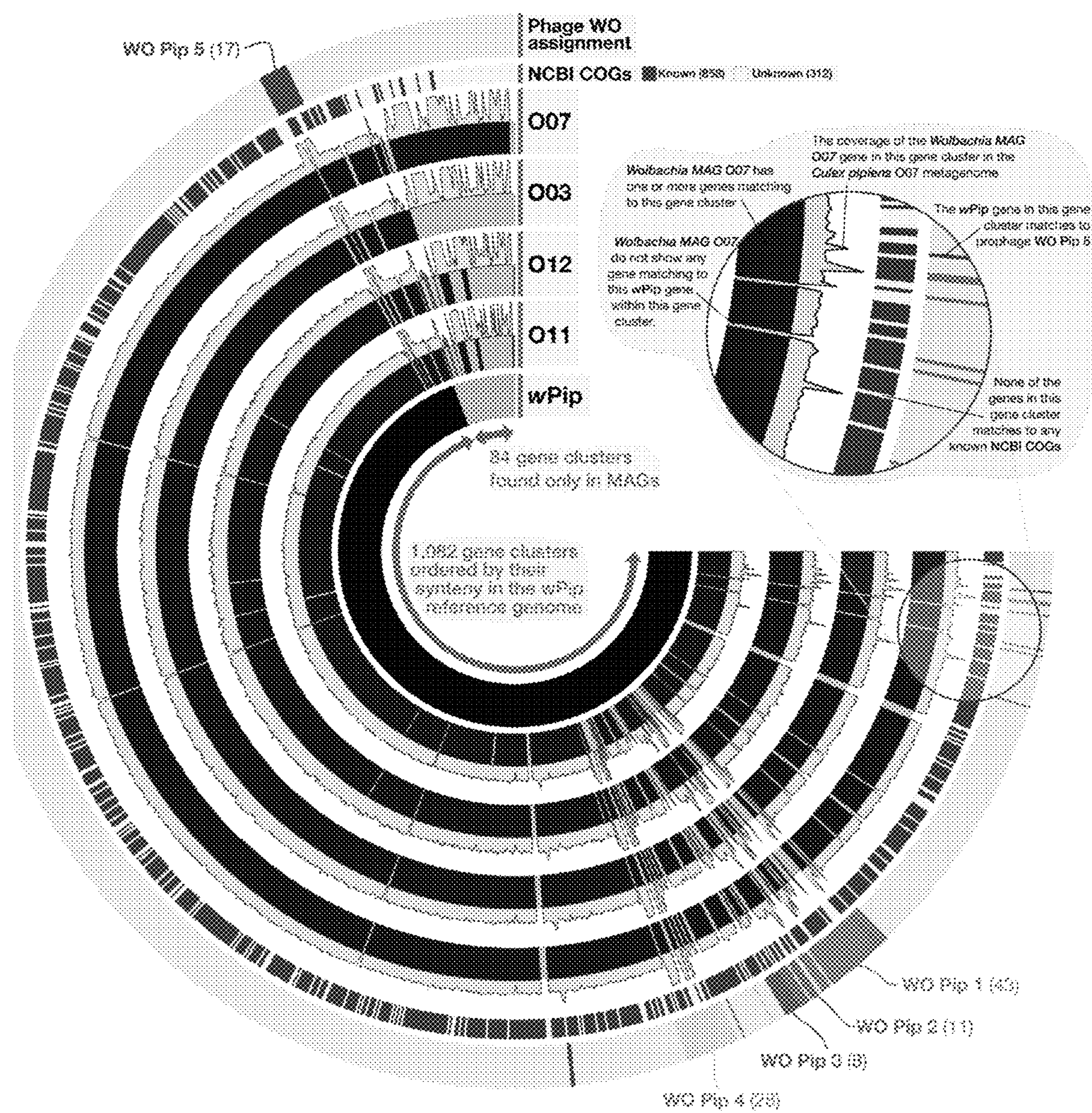
FIG. 3. *Wolbachia* pangenome in the context of wPip genome synteny. The figure shows the presence-absence of 1,166 gene clusters in the pangenome of four *Wolbachia* MAGs and wPip. The gene clusters (i.e., groups of homologous genes based on amino acid sequence identity) are organized based on wPip synteny. Each MAG is represented by two layers, where the first layer indicates the presence or absence of a gene cluster in a given MAG, and the other one shows the average coverage of each *Wolbachia* MAG 007 gene cluster in the corresponding *Culex pipiens* metagenome (the reason read recruitment analysis is done with MAG 007 is because it was the largest *Wolbachia* MAG with the highest number of gene clusters). The second to last layer shows whether genes in a given gene cluster have a match in NCBI's COGs. Most outer layer associates gene clusters with previously identified prophage regions in wPip genome. Number of gene clusters assigned to WO Pip regions are indicated in parenthesis.

Unlike the *Wolbachia* MAGs, wPip is assembled as a single bacterial chromosome. In addition to ordering gene clusters based on their distribution patterns across all genomes (FIG. 5), the wPip genome was used to determine the order of gene clusters in the metapangenome based on the order of wPip genes in the wPip genome (FIG. 3). This 'forced synteny' allowed investigation of the diversity and abundance of phage genes in the context of the five previously identified prophage regions in wPip (FIG. 3). Some gene clusters within prophage regions appeared to be unique to wPip and were not detected in the metagenomes. It is possible these genes were not recovered from the MAGs du to small contig size (that is, contigs were too short to be considered for binning). However, the MAGs often carried upstream and downstream phage genes in these regions, suggesting that while some phage genes were conserved across all genomes, some others differed significantly from their wPip counterparts (FIG. 3). It is possible that a set of new phage-associated genes only found in MAGs (FIG. 3) have functional homologs in wPip. Previous studies indeed show WO genes that have distinct nucleotide sequences yet similar functions (Kent, Funkhouser, et al. 2011). However, it is also possible that some genes detected only in the MAGs at the sequence level may also be encoding unique functions compared to known phage genes; for instance, eukaryotic-like homologs were recently shown as constituents of phage WO (Bordenstein and Bordenstein 2016).

Metagenomic read recruitment revealed between a 1.5 to 5-fold increase in coverage between pWCP and some structural phage genes (e.g., WP0415 and WP0446 Tail genes) in these metagenomes compared to the coverage of the bacterial chromosome in all four *Culex* individuals. The forced synteny organization of gene clusters also revealed that a single prophage region could include both high and low coverage phage genes (FIG. 3). The multi-copy occurrence of pWCP could explain its increased coverage (FIG. 4), and differential coverage regimes for genes within a single prophage region could be explained by at least two different models. In the first model, increased coverage of some prophage genes could be attributed to lytic activity: the prophage genes displaying lower bacterial-like coverage are not part of the virion, while those with higher coverage correspond to phage genes that are replicated and packaged into phage capsids. This lytic model is consistent with the observation of phage particles in *Culex* mosquitoes (Sanogo and Dobson 2006; Wright et al. 1978), observed lytic activity of *Wolbachia* phages in *Nasonia* testes, and the sequencing of WO genomes from purified phage particles (Bordenstein and Bordenstein 2016). The partial replication and packaging of prophage WO genes could result from either a "less than headful" mechanism of packaging, as described in model phages P1 and T4 (Coren, Pierce, and Sternberg 1995; Leffers and Basaveswara Rao 1996), or it could represent active vs. degenerate prophage variants in the wPip chromosome. In the second model, some genes in prophage genomes could be copied throughout the *Wolbachia* chromosome explaining the increase in coverage duc to their multi-copy occurrence. This model is supported by the prophage duplication events observed in the wRi and wSuz genomes (Conner et al. 2017; Klasson et al. 2009) as well as the presence of transposases within and/or flanking prophage variants (Bordenstein and Bordenstein 2016; Klasson et al. 2008) that could enable genomic rearrangement and duplication. These models may not be mutually exclusive, and the system could involve both duplication of prophage genomes and the induction of phage particles.

Circular and Extrachromosomal Nature of pWCP

To further investigate the circular and extrachromosomal nature of pWCP independently of short-read recruitment and assembly-based strategies, long reads were generated from additional *Culex pipiens* complex samples using a MinION sequencer. Since MinION sequencing occurs with no PCR or downstream assembly steps, long-reads that match to pWCP should never be (1) flanked by genomic regions matching to the *Wolbachia* chromosome and (2) longer than the pWCP itself. The MinION sequencing analysis resulted in 14.808 high-quality sequences that were longer than 5,000 nucleotides. While a significant fraction of these reads were eukaryotic contamination and the lambda phage DNA which were used to pad the low-biomass samples, a local BLAST search of artificially-circularized pWCP sequence against long reads revealed 19 that aligned to pWCP with an e-value of <1e-20. Thirteen of these nineteen reads covered >50% of the length of pWCP and contained no other genomic region. In other words, each of the long reads were equal to or shorter than the length of pWCP (FIG. 9(*a*)). Moreover, 6 of these 13 reads were exactly equal to the length of pWCP, covering its entirety with non-identical start positions, confirming its circularity (FIG. 9(*a*)). The final 6 long reads that covered less than 50% of the length of pWCP had specific matches to the IS110 TE (FIG. 9(*b*)); this result is consistent with the multiple occurrences of the IS110 TE in the *Wolbachia* genome, and explains the increase in coverage in metagenomic read recruitment results.

Discussion

Shotgun metagenomes from individual *Culex pipiens* ovary samples allowed de novo reconstruction of the *Wolbachia* genomes from single mosquitoes and compare these metagenome-assembled genomes (MAGs) to each other as well as the reference wPip genome through pangenomic strategies. The data reveal an extensive diversity of previously undetected *Wolbachia* phage and other viral genes, and notably the first indication that *Wolbachia* can harbor a plasmid, shedding new light on the richness of the *Wolbachia* mobilome.

Even though a *Wolbachia* plasmid has not been reported before, evidence was found of its occurrence in metagenomes in previous studies. It is likely that the previous efforts overlooked this element due to computational challenges associated with the assembly of metagenomic short reads. Indeed, the pWCP sequence contained a region of intergenic variable number tandem repeats (VNTR) that differed across individuals in this study, suggesting that the co-assembly of pooled individuals would likely yield fragmented contigs. The same VNTR sequences were found in *C. pipiens* from Australia, Argentina, USA, Italy. Japan, Israel, and Greece (Petridis and Chatzidimitriou 2011), and the presence of pWCP was confirmed in *Culex* samples from countries of Mediterranean basin (Bonneau et al. 2018). The high similarity of pWCP sequences across *Culex* metagenomes in addition to its global prevalence suggest high evolutionary constraints, and a possible role in *Wolbachia* symbiosis. However, efforts to detect the plasmid in other *Wolbachia* strains through screening of available metagenomes from the fly *Drosophila melanogaster*, the planthopper *Laodelphax striatella*, and *Anopheles gambiae* mosquito were not successful.

This work demonstrates that the combination of genome-resolved metagenomics and pangenomic strategies provide an effective computational framework to investigate the diversity and distribution of mobile genetic elements in endosymbionts that are challenging to cultivate. Furthermore, it shows the importance of studying distinct individuals from wild mosquito populations, in parallel to controlled experiments in laboratory settings, to improve the understanding of the *Wolbachia* mobilome. The fragmented nature of *Wolbachia* MAGs in this study emphasizes the critical need for harnessing the power of emerging long-read sequencing technologies to characterize complex genomic variations of *Wolbachia* and its mobilome at finer scales. *Wolbachia* has been so far recalcitrant to genetic modification, but the discovery of pWCP provides new materials and methods for effective genome editing strategies.

Material and Methods

Sample collection. Mosquito specimens were collected using a carbon dioxide mosquito trap located in Languedoc, Herault, France, in May 2017 (Camping l'Europe de Vic La Gardiole, EID Méditerranée). Specimens were transported alive to the lab immediately upon recovery. Adult females were anesthetized for 4 minutes at −20° C. and proceeded to species-level identification. To remove potential contaminants from the insect surface, specimens were gently vortexed for one minute in 1 ml cold (4° C.) 96% ethanol. Specimens were then transferred to a new 1.5 ml tube with 1 ml sterile cold (4° C.) PBS 1× solution, and gently vortexed them again for 10 seconds to avoid DNA precipitation with ethanol. Finally, specimens were transferred onto a sterile microscope slide with sterile PBS 1× on top of a cold plate, and dissected two ovaries from four specimens using sterilized tweezers. Ovary samples were preserved at −80° C. until further processing. *Wolbachia*-free *Culex* individuals were treated with Tetracycline (*Culex quinquefasciatus* S-LAB-TC lines, ISEM, France) and Rifampicin and Oxytetracycline (*Culex pipiens*, Animals Plant Health Agency, UK) antibiotics.

Metagenomic library preparation and sequencing. Total genomic DNA was extracted from each ovary sample, hereafter referred to as O03, O07, O11, and O12, using MoBio PowerFecal DNA Isolation Kit (QIAGEN Inc., Germantown, MD, USA). An E220 Covaris instrument (Covaris, Woburn, MA, USA) was used to sonicate 3.8 ng to 5.7 ng of genomic DNA. Resulting fragments were end-repaired and 3'-adenylated, and used the NEBNext Ultra II DNA Library prep kit for Illumina (New England Biolabs, Ipswich, MA, USA) to add NEXTflex PCR-free barcode adapters (Bioo Scientific, Austin, TX, USA). Ligation products were purified by Ampure XP (Beckmann Coulter, Brea, CA, USA), and PCR-amplified DNA fragments (>200 bp; 2 PCR reactions, 14 cycles) using Illumina adapter-specific primers and NEBNext Ultra II Q5 Master Mix (NEB). After library profile analysis using an Agilent 2100 Bioanalyzer (Agilent Technologies, Santa Clara, CA, USA), and qPCR quantification using the KAPA Library Quantification Kit for Illumina Libraries (KapaBiosystems, Wilmington, MA, USA), the library was sequenced using a HiSeq4000 Illumina sequencer (Illumina, San Diego, CA, USA) at the Genoscope in Evry, France, generating 151 bp paired-end reads. To remove the least reliable data, the raw sequencing results were filtered using cluster intensity and chastity filter as described in (Alberti et al. 2017).

Metagenomic assembly and binning. Illumina-utils v1.4.4 (Eren et al. 2013) was used to quality-filter raw paired-end reads with the program 'iu-filter-quality-minoche' with default parameters, IDBA_UD v1.1.2 (Peng et al. 2012) to assemble paired-end reads into contigs, and Bowtie2 v2.2.9 (Langmead and Salzberg 2012) for all read recruitment analyses. The contigs were processed that are longer than 1,000 nts and read recruitment results with anvi'o v5 (Eren et al. 2015) to recover metagenome-assembled genomes from *C. pipiens* metagenomes. Briefly, the program 'anvi-gen-contigs-database' was used to generate anvi'o contigs databases for each four individual assemblies, during which anvi'o calculates and stores tetranucleotide frequency values and Prodigal v2.6.3 (Hyatt et al. 2010) identifies open reading frames in each contig. Default anvi'o HMM profiles were run on resulting contigs databases using the program 'anvi-run-hmms', and assigned functions to genes using the program anvi-run-nebi-cogs', which searches gene amino acid sequences against the December 2014 release of the Clusters of Orthologous Groups (COGs) database (Tatusoy et al. 2000) using blastp v2.3.0+ (Altschul et al. 1990). The short reads of the contigs recruited from each four individual metagenomes were profiled onto the four assemblies using the program 'anvi-profile', which generates anvi'o profile databases that store the coverage and detection statistics of each contig within each sample independently. Resulting anvi'o profile databases were then merged for each sample using the program 'anvi-merge'. For an initial coarse binning, the CONCOCT (Alneberg et al. 2014) algorithm was used through the program 'anvi-cluster-with-concoct' and confined the number of clusters to five using the parameter '--num-clusters-requested 5'. The program 'anvi-script-get-collection-info' was then used to identify bins with a bacterial population genome, manually refined them to identify bacterial genomes using the program 'anvi-refine', and assigned taxonomy to resulting metagenome-assembled genomes using NCBI's non-redundant protein sequence database with amino acid sequences of core genes. The program 'anvi-refine' allows the identification and refinement of population genome bins through an interactive interface by offering a number of tools including (1) guiding hierarchical clustering dendrograms of contigs (including one based on tetranucleotide frequencies and differential coverage statistics across samples), (2) real-time completion and redundancy estimates of binned contigs based on bacterial single-copy core genes (Campbell et al. 2013), (3) interfaces that display nucleotide-level coverage statistics per gene and contig, (4) functional annotations and synteny of genes, and (5) online sequence homology search options for gene and contig sequences. These tools collectively help minimize the inclusion of non-target contigs (such as eukaryotic contamination) in final bins, especially in complex metagenomes (Delmont and Eren 2016). Except the manual refinement step, the processing of the raw sequencing data was automated with a snakemake (Köster and Rahmann 2012) workflow anvi'o v5 implements, and the code availability section reports necessary configuration files to fully reproduce this analysis.

Pangenomic analysis. The analysis of the *Wolbachia* pangenome followed the workflow outlined in (Delmont and Eren 2018). Briefly, an anvi'o genomes storage database was first generated using the program 'anvi-gen-genomes-storage' to store gene sequences (DNA and amino acid) and functional annotations for each genome. The FASTA files were used of the 4 *Wolbachia* MAGs retrieved in this study using the '--internal-genomes' flag and the *Wolbachia* reference genome of *Culex quinquefasciatus* Pel strain wPip complete genome wPip NC_010981.1.fasta (Klasson et al. 2008) downloaded from NCBI using the --external-genomes.txt. The external genome was beforehand reformatted using the program anvi-script-reformat-fasta and the --simplify-names flag. The same programs were used as for the internal genomes 'anvi-gen-contigs-database', 'anvi-run-hmms' and anvi-run-bcbi-cogs' to identify open reading frames, run hmm profiles and assign function to genes, respectively. The pangenome was computed using the program anvi-pan-genome to identify gene clusters from the genome storage database using the flag '--use-ncbi-blast', and parameters '--minbit 0.5', and '--mcl-inflation 5'. The program (1) uses the blastp program all vs. all to create a graph of similarities between pairs of amino acid sequences (2) removes bad hits using the 'minbit heuristic', (3) uses the Markov Cluster (MCL) algorithm to cluster graphs (4) calculates the occurrence of gene clusters across genomes and the total number of genes they contain, (5) realizes a hierarchical clustering analysis for gene clusters (based on their distribution across genomes) and for genomes (based on shared gene clusters), and finally (6) generates an anvi'o pangenomic database which stores all results for downstream analyses. The pangenome was displayed using anvi-display-pan to visualize gene clusters and their distribution across the five genomes in an interactive interface and created a default collection selecting every gene cluster. The program 'anvi-summarize' was used with the latter collection to obtain a summary of these results, including gene clusters for gene calls of each genome. To identify 'phage-like' gene clusters, a blast database was created of the reference genome wPip NC_010981.1.fasta (Klasson et al. 2008) using makeblastdb and blasted (nr) the five phage fasta files extracted from the latter genome (prophage parameters defined in (Bordenstein and Bordenstein 2016), hereafter referred to as WOPip1-5) against the new db, generating a list of 'phage-like' gene calls. In parallel, to visualize the differential coverage of putative 'phage-like' gene clusters and of the remaining bacterial ones, the program 'anvi-summarize' was used with the flag init-gene-coverages to retrieve the coverage of samples from their profile database.

The wPip 'phage-like' gene clusters were visualized together with the coverage of each gene cluster in representative individual O07 with the program anvi-display-pan using the flag--additional-layer generated with ad hoc R script (Sec code availability section).

Computing the density of single-nucleotide variants per genome and metagenome. To infer the extent of heterogeneity in metagenomes for each *Wolbachia* MAG, the anvi'o program 'anvi-gon-variability-profile' was used to recover single-nucleotide variants from each merged profile without any filters. Only single-nucleotide variants were kept that fall into the context of complete gene calls to minimize erroneous variants that often emerge from mapping artifacts around beginnings and ends of contigs, and calculated the percentage of nucleotide positions in each genome that was not clonal in the metagenome.

Computing the average nucleotide identity between genomes. To compute the level of similarity between the four *Wolbachia* MAGs and the wPip reference genome, the program 'anvi-compute-ani' was used, which called PyANI v0.2.7 (Pritchard et al. 2016) in 'ANIb' mode to align 1 kbp long fragments of the input genome sequences with the NCBI's blastn program to summarize the average nucleotide identity and alignment coverage scores.

PCR amplification of DNA. A set of specific primers was used on the four *Culex pipiens* individuals and three *Wolbachia*-free controls generated by tetracycline treatment using standard techniques. The presence of arthropod DNA was verified by amplifying a ca. 708-bp fragment of the Cytochrome Oxidase I gene from arthropod mitochondria using LCO1490: (5'-GGT CAA CAA ATC ATA AAG ATA TTG G-3') (SEQ ID NO: 11) and HCO2198 (S'-TAA ACT TCA GGG TGA CCA AAA AAT CA-3') (SEQ ID NO:12) primers (Folmer et al. 1994). The presence of *Wolbachia*

DNA was checked by PCR amplifying a ca. 438 bp fragment of the *Wolbachia* 16S rDNA gene using Wspec-F: CAT ACC TAT TCG AAG GGA TAG (SEQ ID NO: 13) and Wspec-R: AGC TTC GAG TGA AAC CAA TTC (SEQ ID NO: 14) primers (Werren and Windsor 2000). The PCR conditions for both sets of primers included a temperature regime of 2 min at 94° C., followed by 29 cycles of 30 s at 94° C., 45 s at 49° C., 1 min at 72° C. and a final elongation of 10 min at 72° C. To detect the circularity of the plasmid-like genome, new primers were designed (listed in Results) and the following cycling parameters were used: 2 min at 95° C., followed by 34 cycles of (94° C. for 30 s, 58° C. for 45 s, and 72° C. for 2 min) with a final elongation of 5 min at 72° C. Finally, to confirm presence of the IS110 transposase, primers were used as described in results section under the following PCR conditions: 2 min at 95° C., followed by 34 cycles of (94° C. for 30 s, 55° C. for 45 s, and 72° C. for 30 s) and a final elongation of 5 min at 72° C. Amplifications by polymerase chain reaction (PCR) were performed using Platinum Taq DNA Polymerase High Fidelity (5U/μl, Invitrogen).

Plasmid Characterization. The Glimmer software within Geneious v8.1.9 (Biomatters, Ltd) was used to identify Open reading frames (ORFs), and used the NCBI databases for non-redundant protein sequences and conserved domains (Marchler-Bauer et al. 2002), SMART (Letunic and Bork 2018), and HHPPred (Zimmermann et al. 2018) (including SCOPe, Pfam, and COG) to manually annotate putative functions based on amino acid sequence homology searches. The IS finder platform was used for IS homology search. The nucleotide analysis plugin in Geneious for EMBOSS identified and illustrated the extragenic palindrome in the plasmid.

REFERENCES CITED IN THIS EXAMPLE

Alberti, Adriana et al. 2017. "Viral to Metazoan Marine Plankton Nucleotide Sequences from the Tara Oceans Expedition." *Scientific Data* 4:1-20.

Alneberg, Johannes et al. 2014. "Binning Metagenomic Contigs by Coverage and Composition." *Nature Methods* 11:1144.

Altschul, S. F., W. Gish, W. Miller, E. W. Myers, and D. J. Lipman. 1990. "Basic Local Alignment Search Tool." *Journal of Molecular Biology* 215 (3): 403-10.

Andrews, Elizabeth S., Philip R. Crain, Yuqing Fu, Daniel K. Howe, and Stephen L. Dobson. 2012. "Reactive Oxygen Species Production and *Brugia pahangi* Survivorship in *Aedes polynesiensis* with Artificial *Wolbachia* Infection Types." *PLOS Pathogens* 8 (12).

Ant, Thomas H., Christie S. Herd, Vincent Geoghegan, Ary A. Hoffmann, and Steven P. Sinkins. 2018. "The *Wolbachia* Strain WAu Provides Highly Efficient Virus Transmission Blocking in *Aedes aegypti.*" *PLOS Pathogens* 14 (1): 1-19.

Atyame, Célestine M. et al. 2014. "*Wolbachia* Divergence and the Evolution of Cytoplasmic Incompatibility in *Culex pipiens.*" *PLOS ONE* 9 (1): 21-26.

Baldridge, Gerald D., Nicole Y. Burkhardt, Roderick F. Felsheim, Timothy J. Kurtti, and Ulrike G. Munderloh. 2007. "Transposon Insertion Reveals PRM, a Plasmid of *Rickettsia monacensis.*" *Applied and Environmental Microbiology* 73 (15): 4984-95.

Beckmann, John F., Judith A. Ronau, and Mark Hochstrasser. 2017. "A *Wolbachia* Deubiquitylating Enzyme Induces Cytoplasmic Incompatibility." *Nature Microbiology* 2:17007.

Bian, Guowu et al. 2013. "*Wolbachia* Invades *Anopheles stephensi* Populations and Induces Refractoriness to *Plasmodium* Infection." *Science* 340 (6133).

Blagrove, M. S. C., C. Arias-Goeta, A. B. Failloux, and S. P. Sinkins. 2012. "*Wolbachia* Strain WMel Induces Cytoplasmic Incompatibility and Blocks Dengue Transmission in *Aedes albopictus.*" *Proceedings of the National Academy of Sciences* 109 (1): 255-60.

Bonneau, Manon et al. 2018. "*Culex pipiens* Crossing Type Diversity Is Governed by an Amplified and Polymorphic Operon of *Wolbachia.*" *Nature Communications* 9 (1): 319.

Bordenstein, S. R. and J. H. Werren. 2007. "Bidirectional Incompatibility among Divergent *Wolbachia* and Incompatibility Level Differences among Closely Related *Wolbachia* in *Nasonia.*" *Heredity* 99 (3): 278-87.

Bordenstein, Sarah R. and Seth R. Bordenstein. 2016. "Eukaryotic Association Module in Phage WO Genomes from *Wolbachia.*" *Nature Communications* 7:1-10.

Bordenstein, Seth R. and Jennifer J. Wernegreen. 2004. "Bacteriophage Flux in Endosymbionts (*Wolbachia*): Infection Frequency, Lateral Transfer, and Recombination Rates." *Molecular Biology and Evolution* 21 (10): 1981-91.

Boyer, Sébastien, Elodie Calvez, Thais Chouin-Carneiro, Diawo Diallo, and Anna Bella Failloux. 2018. "An Overview of Mosquito Vectors of Zika Virus." *Microbes and Infection.*

Burkhardt, Nicole Y. et al. 2011. "Development of Shuttle Vectors for Transformation of Diverse *Rickettsia* Species." *PLOS ONE* 6 (12).

Campbell, J. H. et al. 2013. "UGA Is an Additional Glycine Codon in Uncultured SR1 Bacteria from the Human Microbiota." *Proceedings of the National Academy of Sciences* 110 (14): 5540-45.

Cerveau, Nicolas, Sébastien Leclercq, Elodie Leroy, Didier Bouchon, and Richard Cordaux. 2011. "Short- and Long-Term Evolutionary Dynamics of Bacterial Insertion Sequences: Insights from *Wolbachia* Endosymbionts." *Genome Biology and Evolution* 3 (1): 1175-86.

Cerveny, Lukas et al. 2013. "Tetratricopeptide Repeat Motifs in the World of Bacterial Pathogens: Role in Virulence Mechanisms." *Infection and Immunity* 81 (3): 629-35.

Chafee, Meghan E., Daniel J. Funk, Richard G. Harrison, and Seth R. Bordenstein. 2010. "Lateral Phage Transfer in Obligate Intracellular Bacteria (*Wolbachia*): Verification from Natural Populations." *Molecular Biology and Evolution* 27 (3): 501-5.

Conner, William R. et al. 2017. "Genome Comparisons Indicate Recent Transfer of WRi-like *Wolbachia* between Sister Species *Drosophila suzukii* and *D. subpulchrella*." Ecology and Evolution 7 (22): 9391-9404.

Coren, Jonathon S., James C. Pierce, and Nat Sternberg. 1995. "Headful Packaging Revisited: The Packaging of More than One DNA Molecule into a Bacteriophage P1 Head." *Journal of Molecular Biology* 249 (1): 176-84.

Delmont, Tom O. and A. Murat Eren. 2016. "Identifying Contamination with Advanced Visualization and Analysis Practices: Metagenomic Approaches for Eukaryotic Genome Assemblies." *PeerJ* 4: e1839.

Delmont, Tom O. and A. Murat Eren. 2018. "Linking Pangenomes and Metagenomes: The Prochlorococcus Metapangenome." *PeerJ* 6: e4320.

Eren, A. Murat et al. 2015. "Anvi'o: An Advanced Analysis and Visualization Platform for 'omics Data." *PeerJ* 3: e1319.

Eren, A. Murat, Joseph H. Vineis, Hilary G. Morrison, and Mitchell L. Sogin. 2013. “A Filtering Method to Generate High Quality Short Reads Using Illumina Paired-End Technology.” *PLOS ONE* 8 (6): 6-11.

Ferree, Patrick M. et al. 2005. “*Wolbachia* Utilizes Host Microtubules and Dynein for Anterior Localization in the *Drosophila* Oocyte.” *PLOS Pathogens* 1 (2): 0111-24.

Flores, Heather A. and Scott L. O’Neill. 2018. “Controlling Vector-Borne Diseases by Releasing Modified Mosquitoes.” *Nature Reviews Microbiology* 1.

Folmer, Ole, Michael Black, Hoeh Wr, R. Lutz, and Robert Vrijenhoek. 1994. *DNA Primers for Amplification of Mitochondrial Cytochrome C Oxidase Subunit I from Diverse Metazoan Invertebrates.*

Funkhouser-Jones, Lisa J., Edward J. van Opstal, Ananya Sharma, and Seth R. Bordenstein. 2018. “The Maternal Effect Gene Wds Controls *Wolbachia* Titer in *Nasonia.*” *Current Biology* 28 (11): 1692-1702.e6.

Gould, Ernest, John Pettersson, Stephen Higgs, Remi Charrel, and Xavier de Lamballerie. 2017. “Emerging Arboviruses: Why Today?” *One Health* 4 (April): 1-13.

Harms, Alexander, Ditlev Egeskov Brodersen, Namiko Mitarai, and Kenn Gerdes. 2018. “Toxins, Targets, and Triggers: An Overview of Toxin-Antitoxin Biology.” *Molecular Cell* 1-17.

Hedges, Lauren M., Jeremy C. Brownlie, Scott L. O’Neill, and Karyn N. Johnson. 2008. “*Wolbachia* and Virus Protection in Insects.” *Science* 322 (5902): 702.

Hyatt, Doug et al. 2010. “Prodigal: Prokaryotic Gene Recognition and Translation Initiation Site Identification.” *BMC Bioinformatics* 11.

Ishmael, Nadeeza et al. 2009. “Extensive Genomic Diversity of Closely Related *Wolbachia* Strains.” *Microbiology* 155 (7): 2211-22.

Iturbe-Ormaetxe, Iñaki, Megan Woolfit, Edwige Rancès, Anne Duplouy, and Scott L. O' Neill. 2011. “A Simple Protocol to Obtain Highly Pure *Wolbachia* Endosymbiont DNA for Genome Sequencing.” *Journal of Microbiological Methods* 84 (1): 134-36.

Jeffries, Claire L. and Thomas Walker. 2016. “*Wolbachia* Biocontrol Strategies for Arboviral Diseases and the Potential Influence of Resident *Wolbachia* Strains in Mosquitoes.” *Current Tropical Medicine Reports* 3 (1): 20-25.

Joubert, D. Albert et al. 2016. “Establishment of a *Wolbachia* Superinfection in *Aedes aegypti* Mosquitoes as a Potential Approach for Future Resistance Management.” *PLOS Pathogens* 12 (2): 1-19.

Joubert, Dirk Albert and Scott L. O’Neill. 2017. “Comparison of Stable and Transient *Wolbachia* Infection Models in *Aedes aegypti* to Block Dengue and West Nile Viruses.” *PLOS Neglected Tropical Diseases* 11 (1): 1-14.

El Karkouri, Khalid, Pierre Pontarotti, Didier Raoult, and Pierre Edouard Fournier. 2016. “Origin and Evolution of Rickettsial Plasmids.” *PLOS ONE* 11 (2): 1-17.

Kent, Bethany N., Leonidas Salichos, et al. 2011. “Complete Bacteriophage Transfer in a Bacterial Endosymbiont (*Wolbachia*) Determined by Targeted Genome Capture.” *Genome Biology and Evolution* 3 (1): 209-18.

Kent, Bethany N., Lisa J. Funkhouser, Shefali Setia, and Seth R. Bordenstein. 2011. “Evolutionary Genomics of a Temperate Bacteriophage in an Obligate Intracellular Bacteria (*Wolbachia*).” *PLOS ONE* 6 (9).

Klasson, L. et al. 2009. “The Mosaic Genome Structure of the *Wolbachia* WRi Strain Infecting *Drosophila Simulans.*” *Proceedings of the National Academy of Sciences* 106 (14): 5725-30.

Klasson, Lisa et al. 2008. “Genome Evolution of *Wolbachia* Strain WPip from the *Culex pipiens* Group.” *Molecular Biology and Evolution* 25 (9): 1877-87.

Konieczny, Igor, Katarzyna Bury, Aleksandra Wawrzycka, and Katarzyna Wegrzyn. 2014. “Iteron Plasmids.” *Microbiology Spectrum* 2 (6): 1-16.

Köster, Johannes and Sven Rahmann. 2012. “Snakemake—a Scalable Bioinformatics Workflow Engine.” *Bioinformatics* 28 (19): 2520-22.

Langmead, Ben and Steven L. Salzberg. 2012. “Fast Gapped-Read Alignment with Bowtie 2.” *Nature Methods* 9:357.

Laven, H. 1967. “A Possible Model for Speciation by Cytoplasmic Isolation in the *Culex pipiens* Complex.” *Bulletin of the World Health Organization* 37 (2): 263-66.

Leffers, Gerald and Venigalla Basaveswara Rao. 1996. “A Discontinuous Headful Packaging Model for Packaging Less Than Headful Length DNA Molecules by Bacteriophage T4.” *Journal of Molecular Biology* 258 (5): 839-50.

LePage, Daniel and Seth R. Bordenstein. 2013. “*Wolbachia*: Can we Save Lives with a Great Pandemic?” *Trends in Parasitology* 29 (8): 385-93.

LePage, Daniel P. et al. 2017. “Prophage WO Genes Recapitulate and Enhance *Wolbachia*-Induced Cytoplasmic Incompatibility.” *Nature* 543:243.

Letunic, Ivica and Peer Bork. 2018. “20 Years of the SMART Protein Domain Annotation Resource.” *Nucleic Acids Research* 46 (D1): D493-96.

Lo, Nathan, Maurizio Casiraghi, Emanuela Salati, Chiara Bazzocchi, and Claudio Bandi. 2002. “How Many *Wolbachia* Supergroups Exist?” *Molecular Biology and Evolution* 19 (3): 341-46.

Marchler-Bauer, Aron et al. 2002. “CDD: A Database of Conserved Domain Alignments with Links to Domain Three-Dimensional Structure.” *Nucleic Acids Research* 30 (1): 281-83.

McMeniman, Conor J. et al. 2009. “Stable Introduction of a Life-Shortening <Em>*Wolbachia*</Em> Infection into the Mosquito <Em>*Aedes aegypti*</Em>” *Science* 323 (5910): 141 LP-144.

Ogata, Hiroyuki et al. 2005. “The Genome Sequence of *Rickettsia felis* Identifies the First Putative Conjugative Plasmid in an Obligate Intracellular Parasite.” *PLOS Biology* 3 (8).

Pan, Xiaoxiao, Anja Lührmann, Ayano Satoh, Michelle A. Laskowski-Arce, and Craig R. Roy. 2008. “Ankyrin Repeat Proteins Comprise a Diverse Family of Bacterial Type IV Effectors.” *Science* (*New York, N.Y.*) 320 (5883): 1651-54.

Peng, Yu, Henry C. M. Leung, S. M. Yiu, and Francis Y. L. Chin. 2012. “IDBA-UD: A de Novo Assembler for Single-Cell and Metagenomic Sequencing Data with Highly Uneven Depth.” *Bioinformatics* 28 (11): 1420-28.

Petridis, Michael and Dimitrios Chatzidimitriou. 2011. “Characterization of an Intergenic Polymorphic Site (Pp-HC1A_5) in *Wolbachia pipientis* (WPip).” *Molecular Ecology Resources* 11 (4): 753-56.

Pritchard, Leighton, Rachel H. Glover, Sonia Humphris, John G. Elphinstone, and Ian K. Toth. 2016. “Genomics and Taxonomy in Diagnostics for Food Security: Soft-Rotting Enterobacterial Plant Pathogens.” *Anal. Methods* 8 (1): 12-24.

Riegler, Markus, Iñaki Iturbe-Ormaetxe, Megan Woolfit, Wolfgang J. Miller, and Scott L. O’Neill. 2012. “Tandem Repeat Markers as Novel Diagnostic Tools for High Resolution Fingerprinting of *Wolbachia*." *BMC Microbiology* 12 (SUPPL. 1):S12.

Salzberg, Steven L., Daniela Puiu, Daniel D. Sommer, Vish Nene, and Norman H. Lee. 2009. "Genome Sequence of the *Wolbachia* Endosymbiont of *Culex quinquefasciatus* JHB." *Journal of Bacteriology* 191 (5): 1725.

Sanogo, Yibayiri O. and Stephen L. Dobson. 2006. "WO Bacteriophage Transcription in *Wolbachia*-Infected *Culex pipiens." Insect Biochemistry and Molecular Biology* 36 (1): 80-85.

Serbus, Laura R. and William Sullivan. 2007. "A Cellular Basis for *Wolbachia* Recruitment to the Host Germline." *PLOS Pathogens* 3 (12): 1930-37.

Shao, Yucheng et al. 2011. "TADB: A Web-Based Resource for Type 2 Toxin-Antitoxin Loci in Bacteria and Archaea." *Nucleic Acids Research* 39 (SUPPL. 1): 606-11.

Shen, Xiaodong et al. 2012. "Functional Identification of the DNA Packaging Terminase from *Pseudomonas aeruginosa* Phage PaP3." *Archives of Virology* 157 (11): 2133-41.

Shragai, Talya, Blanka Tesla, Courtney Murdock, and Laura C. Harrington. 2017. "Zika and Chikungunya: Mosquito-Borne Viruses in a Changing World." *Annals of the New York Academy of Sciences* 1399 (1): 61-77.

Shropshire, J. Dylan, Jungmin On, Emily M. Layton, Helen Zhou, and Seth R. Bordenstein. 2018. "A Single Prophage WO Gene Rescues Cytoplasmic Incompatibility in *Drosophila melanogaster." BioRxiv* (21): 300269.

Singhal, Kopal and Sujata Mohanty. 2018. "Comparative Genomics Reveals the Presence of Putative Toxin-Antitoxin System in *Wolbachia* Genomes." *Molecular Genetics and Genomics* 293 (2): 525-40.

Siozios, Stefanos et al. 2013. "Draft Genome Sequence of The." *Genome Annuncements* 1 (1): e00032-13.

Sun, Ling V et al. 2001. "Determination of *Wolbachia* Genome Size by Pulsed-Field Gel Electrophoresis." *Journal of Bacteriology* 183 (7): 2219-25.

Tatusov, Roman L., Michael Y. Galperin, Darren A. Natale, and Eugene V Koonin. 2000. "The COG Database: A Tool for Genome-Scale Analysis of Protein Functions and Evolution." *Nucleic Acids Research* 28 (1): 33-36.

Teixeira, Luís, Álvaro Ferreira, and Michael Ashburner. 2008. "The Bacterial Symbiont *Wolbachia* Induces Resistance to RNA Viral Infections in *Drosophila melanogaster." PLOS Biology* 6 (12): 2753-63.

Turelli, Michael. 1994. "EVOLUTION OF INCOMPATIBILITY-INDUCING." 48 (5): 1500-1513.

Turelli, Michael and Ary A. Hoffmann. 1991. "Rapid Spread of an Inherited Incompatibility Factor in California *Drosophila." Nature* 353 (6343): 440-42.

Werren, J. H. and D. M. Windsor. 2000. "*Wolbachia* Infection Frequencies in Insects: Evidence of a Global Equilibrium?" *Proceedings of the Royal Society B: Biological Sciences* 267 (1450): 1277-85.

Werren, John H. 1997. "Biology of *Wolbachia." Annu. Rev. Entomol.* 124 (42): 587-609.

Wood, David O. et al. 2012. "Establishment of a Replicating Plasmid in *Rickettsia prowazekii." PLOS ONE* 7 (4): 1-6.

Woolfit, Megan et al. 2013. "Genomic Evolution of the Pathogenic *Wolbachia* Strain, WMelPop." *Genome Biology and Evolution* 5 (11): 2189-2204.

Wright, John D., Fritiof S. Sjostrand, Joseph K. Portaro, and A. Ralph Barr. 1978. "The Ultrastructure of the *Rickettsia*-like Microorganism *Wolbachia pipientis* and Associated Virus-like Bodies in the Mosquito *Culex pipiens." Journal of Ultrasructure Research* 63 (1): 79-85.

Zimmermann, Lukas et al. 2018. "A Completely Reimplemented MPI Bioinformatics Toolkit with a New HHpred Server at Its Core." *Journal of Molecular Biology* 430 (15): 2237-43.

Example 2. Plasmid Transformation of *Wolbachia*

Plasmid Transformation of *Wolbachia* within Eukaryotic Host Cells

1. Generate desired plasmid construct with promoter, heterologous nucleic acid sequence (heterologous gene) and selectable marker(s).
2. Complex G4 dendrimers with plasmid DNA by vortexing components in sterile water and incubating at room temperature.
3. Resuspend dendrimer complex in Schneider's *Drosophila* media lacking FBS or glutamine.
4. Overlay dendrimer solution onto confluent *Wolbachia*-infected insect cells and incubate.
5. Wash cells and add Schneider's with 10% FBS.
6. After 24 hours, maintain cultures in the presence of antibiotic (i.e., tetracycline).

Plasmid Transformation of Host-Free *Wolbachia*

1. Purify *Wolbachia* (Gamston C, Rasgon J. J Vis Exp. 2007; (5): 223; Iturbe-Ormaetxe I, et. al. J Microbiol Methods. 2011; 84 (1): 134-6; Rasgon J L, et. al. Appl Environ Microbiol. 2006; 72 (11): 6934-7) and suspend in Schneider's *Drosophila* media lacking FBS or glutamine.
2. Gently mix with dendrimer complex and incubate at room temperature.
3. Grow host cells (i.e., *Drosophila* S2) to ~80% confluence.
4. Remove media without disturbing cell monolayer.
5. Add 2 ml of suspended *Wolbachia*/dendrimer complex onto cell monolayer.
6. Centrifuge plates at 2,500×g for 1 hour at 15° C.
7. Allow cells to sit overnight.
8. Wash cells and add Schneider's with 10% FBS.
9. After 24 hours, maintain cultures in the presence of antibiotic (i.e., tetracycline).

Transfer of pWCP to Naïve *Wolbachia* Hosts

1. Purify pWCP from donor *Wolbachia* strain.
2. Transfer pWCP to recipient *Wolbachia* using one of the following methods:
   a. Grow *Wolbachia*-infected host cells to ~80% confluence and add purified plasmid.
   b. Purify *Wolbachia* cells, add purified plasmid and re-infect host cells.
   c. Inject insect abdomens (or embryos) with suspended plasmid.
   d. Deliver plasmid into mosquito cell using gene gun (transfection by particle bombardment).

Figure 7:
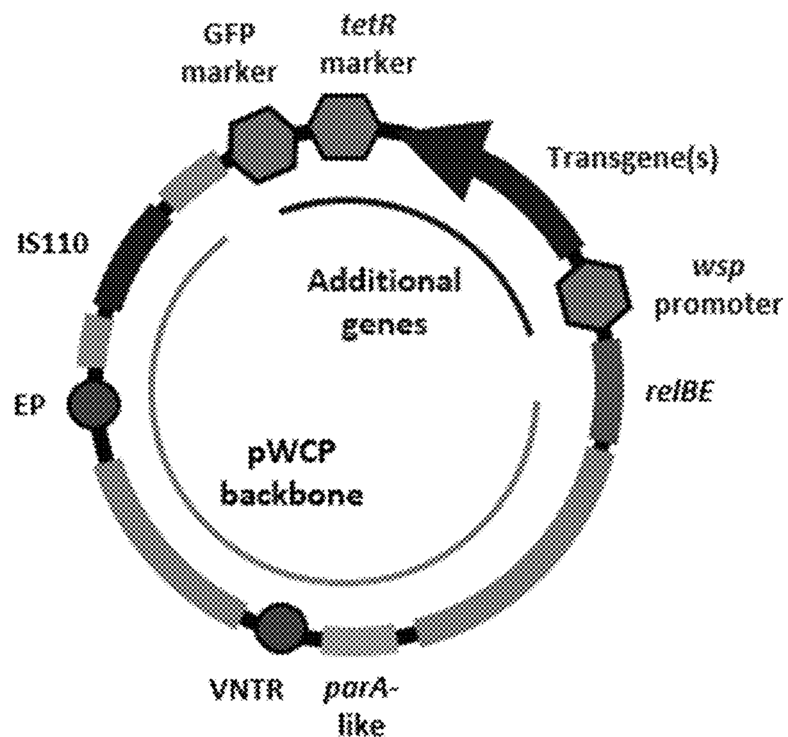
FIG. 7. Schematic of a plasmid comprising pWCP backbone with a single relBE operon, transgene(s), and marker(s).
Figure 8:
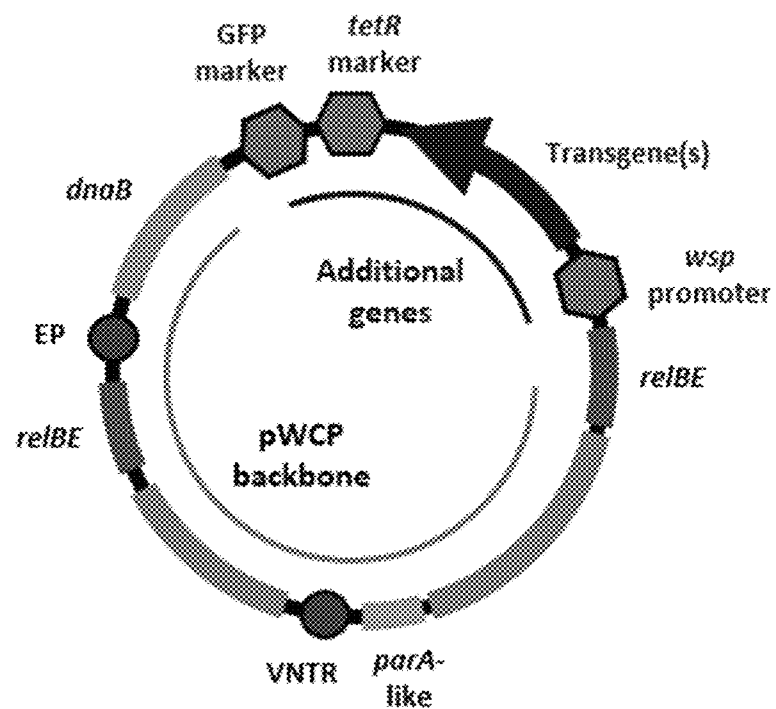
FIG. 8. Schematic of a plasmid comprising pWCP backbone with dnaB, transgene(s), and marker(s).

Additional schematics of plasmids disclosed herein are shown, for example, in FIG. 6, FIG. 7, and FIG. 8.

```
SEQUENCES
IS110, transposase:
                                    SEQ ID NO: 1
ATGATTACATCTTATCAAAATTTTATTGGCATTGA

TATCGGGAAATTTAAAAATGTTGTTGCAGTTCACG

AACAGAAGAATACTGTAGGATTTGACAATAATACT
```

-continued

TCTGGCTGGCAACAATTGTTTCAAAAGTTTTCAGA

TATCCTACCTAATTCTTTAGTAACTTTAGAAAATA

CAGGAAAGTATGAGCTTGGTTTATTACATTTTCTT

GTTGACAAAAATATTGCCACACATCGAGCTAATAC

CCGTAAAGTAAAAAGCTTTATCTTGTCTCACGGAA

CTTTAGCAAAGTCTGATAAATCAGATGCAAGAGCT

CTTGCTCAATATGGATTTGAACGCCACAGCACTAT

CTCTCTATTTGTACCCACTTTTGAAAATCAATCAA

CCTTGGTTGCACTTTGTCAACGTCGTGATGACATT

ACGCAAATGAGAGCTCAGGAAAAATGTAGACTGGC

AGCACCTGAAAATGACCATATAAAAGAAAGTTGTC

AAAAAACTATCGAATTCTTTAATATTCAAATAGAT

GAACTCAATAATACTATACAAAAAATTATTGATGA

AAGCCGTGAGTTACAACAACGTCAAAAAATCCTAA

AAACAGTTCCTGGAATAGGTCCAAAGTTATCTCAA

GATTTTCTCTGTTTAATGCCAGAGCTTGGTTACTT

AAGCAGGAGAGAAGTTGCAAGCCTTGCTGGGGTTG

CACCTTATCCAAAAGAAAGTGGTAAAACTATTGGA

TACCGAAGAATAACAGGTGGTAGAAGCAATGTTCG

TGCAAAACTTTTTACATCTGCCATGGCTGCTGCAA

AGTCCAAATCTGTACTTGGTGCCTTTTATTCTAAG

CTTGTTGAAAGTGGTAAGAAGAAGATGGTAGCTAT

AACAGCTCTAATGCGTAAAATTATAGTAATTGCTA

ACGCAAGGCTTAAAGAAGCAATTAATTTGAATATT

TAA

IS110 transposase:

SEQ ID NO: 2

MITSYQNFIGIDIGKFIKNVVAVHEQKNTVGFDNN

TSGWQQLFQKFSDILPNSLVTLENTGKYELGLLHF

LVDKNIATHRANTRKVKSFILSHGTLAKSDKSDAR

ALAQYGFERHSTISLFVPTFENQSTLVALCQRRDD

ITQMRAQEKCRLAAPENDHIKESCQKTIEFFNIQI

DELNNTIQKIIDESRELQQRQKILKTVPGIGPKLS

QDFLCLMPELGYLSRREVASLAGVAPYPKESGKTI

GYRRITGGRSNVRAKLFTSAMAAAKSKSVLGAFYS

KLVESGKKKMVAITALMRKIIVIANARLKEAINLN

I pWCP:

SEQ ID NO: 3

AATATTGTAAGTCAAAAATATGATATAAAGGAAAT

AAGAGGGAAAGATAACCCTACTCACTATAGGAATA

GGGTTATCACGGGCGTGTGCGACCGGCAGAATATT

-continued

GGTATTACAACCGTGTCCATCAAGGTACACTAGCC

CATCTCTCGATACGTTTGAATAGTTGTGTGGGACA

TGTATATGCACCCGTTTACAATCTTAAATTAATTA

AACTATCGAGGTTATAATGATTACATCTTATCAAA

ATTTTATTGGCATTGATATCGGGAAATTTAAAAAT

GTTGTTGCAGTTCACGAACAGAAGAATACTGTAGG

ATTTGACAATAATACTTCTGGCTGGCAACAATTGT

TTCAAAAGTTTTCAGATATCCTACCTAATTCTTTA

GTAACTTTAGAAAATACAGGAAAGTATGAGCTTGG

TTTATTACATTTTCTTGTTGACAAAAATATTGCCA

CACATCGAGCTAATACCCGTAAAGTAAAAAGCTTT

ATCTTGTCTCACGGAACTTTAGCAAAGTCTGATAA

ATCAGATGCAAGAGCTCTTGCTCAATATGGATTTG

AACGCCACAGCACTATCTCTCTATTTGTACCCACT

TTTGAAAATCAATCAACCTTGGTTGCACTTTGTCA

ACGTCGTGATGACATTACGCAAATGAGAGCTCAGG

AAAAATGTAGACTGGCAGCACCTGAAAATGACCAT

ATAAAAGAAAGTTGTCAAAAAACTATCGAATTCTT

TAATATTCAAATAGATGAACTCAATAATACTATAC

AAAAAATTATTGATGAAAGCCGTGAGTTACAACAA

CGTCAAAAAATCCTAAAAACAGTTCCTGGAATAGG

TCCAAAGTTATCTCAAGATTTTCTCTGTTTAATGC

CAGAGCTTGGTTACTTAAGCAGGAGAGAAGTTGCA

AGCCTTGCTGGGGTTGCACCTTATCCAAAAGAAAG

TGGTAAAACTATTGGATACCGAAGAATAACAGGTG

GTAGAAGCAATGTTCGTGCAAAACTTTTTACATCT

GCCATGGCTGCTGCAAAGTCCAAATCTGTACTTGG

TGCCTTTTATTCTAAGCTTGTTGAAAGTGGTAAGA

AGAAGATGGTAGCTATAACAGCTCTAATGCGTAAA

ATTATAGTAATTGCTAACGCAAGGCTTAAAGAAGC

AATTAATTTGAATATTTAAAATTTACATAGCAGTA

ATTGAAATGAATATTGTGAATAAGCACGTCCGCAC

AAACTTAAAGTGCTTATTCACAATAGCTTAAACGG

AAATTGTTGCAGCAGCTGTTTGATATAGAATTCTG

TTTCTATGACAAACGGGTTTTTATTATCTATATGG

TTGGGTAAAGTTGCAAAATTATACAAATAAAAAAT

TTAAAAAACATAGTTGATGGAGCTTCTCTACCAAG

GATTAAATGAATTAGCCTTTTTAAATCTCCTTGTC

GATAGTTCAGGAAGTATGGATTTAAATGTGCTGAG

AAGAAAGATTGCATCAATCTGTGAAAAACACAGCA

TCAAATGCATCTACATTGACTATCTGCAGCTACTC

-continued

AGAGGATCAGGAAGAACAGAGAACAGAACGCTTGA

AGTGACAGAAATCAGCAGAACATTAAAGAACATCG

CTAAAGACTTTGCAGTTCCTGTTGTCGCGCTATCA

CAAATTAGTCGCAGAGTGGAAGAAAGGCAAAACAA

AAGACCGCAACTAGCAGACCTGCGAGAGTCAGGGA

GCATCGAACAAGACGCTGATATAGTTTTACTACTC

TACAGAGACAGCTACTATAAGATAGGCTCTAATAA

CGAACTAGAGATAAATGTCGCAAAGAATAGAAGTG

GCTCAACCGGTAAAGTTACAGTGCGCTATCAAGTT

AATACTGGAAGAATATTGATTTAACGTTTTAGTAA

GTCTAATATTGCCTGATTGTAAATGTTATCTCTAT

GTCCTATTGAGACAACAGTTACTATACGTTTTGCA

GTATCTACACGGTAGACGATACGATAATCACCCAC

TCGTATTCTGCGATATCCCTTTAATCTATTGCGTA

ATGATACACCGCTAGCAATAGGATCAGTCTCAAGA

TATTCTTTTATTGCTTCTTTAATACTTGGTTTAAT

GTCTTCTGGTAAGGAAGGTATATTCCTCTTAATAA

CATGTTTGAGATATTTGATAGTATAACGTTTATTT

CCAGATGTCTTCACTATCTTCTATTTCTTCCGCAT

CATCATCACTTAATTCTCTAATAATTTTAGAAAAC

GCAATGTCTTCTGCTTCAAGCTCAATTGCTTCTTT

GACTAACTTTCCTGCTAATTTTTGAACAGACTGCT

TGGTAGCTTTAGCTAGTTCAATAAGGTGCTGTGAA

GTTTCTGTATCGAAGGTTACATTAATCCTTGAATC

TGCCATAAGTTTTACCAAAGTTTATCAGTAATTAT

ATAATATTTTCCTGAATTTTTCAATAAAGATCTCT

CCTAAACTTAGAAGAGATCTTTATGGTTAAACTAC

TTTGATTTGCTCGAAGTCTGTAAAGCAAAGTATGT

GCTTGAATTCACGAACGAAGAAGGTAATGAACCCC

CTAACTGTTCTAGCTCTCTCAGAGAAAGCTTCCCT

TCCATAACACACCTTGCGTTTTTCTCTTCTTGTGT

CTCAGAAATTTTTTGATTATACTTTGAACACGAGG

CACTCTCATCATTTCTTTTAAAATCTTTCATAATT

AATCCCTTAAAGCTATAAAAAATACTAAACTAGTA

TACAGTAAAACATAATACTTTAGCAAGTTACTATC

CCAGTTGATTTAGTGTTTTCTCAGATATTAAACCT

TTTTTTAGTAATAATGTATTTTTCACTTCTCTTAA

ATCTGTAGAAGGACCTCCAAGTTGATCCACAACTT

CTGAAATATCCCATTTAGTCGGATCTGGCATATGC

GGTAAAAGCCTTCCCCATGAACCTCCTAATTGCTC

-continued

TAACTCTTTTTCAGGATATTTTTCCTGCTGCACCT

GTGAGCCCAATTCTTTAAGTGCAAACCTTGCCTCT

GGACTTTTTGCTATAAAATCCTCTACTTTATTAGC

TCCTTCAGATAAAAGCTTTACCTCCTCAGAACTTT

CTTGTTGCAATTGTGACGCTAACGCTTCATACAAA

GGCTTTGCTTTACCTTGAGGACCTAATATTACCTC

TGTATTTGCTTGCAACTGTTCTTCAGTAATACCAT

TTCTTTCAATAAACTCGACAGGCTTGTCAGAATGA

ATAAGAACTTTGATCTTACATTCTTTTCCTTCAAC

TTCCCAATTAATAGTCATTTCATATGAATCATGAG

CTACCTCATATATTCTTGTTCCATCCTCACAAAGG

GACAAACGTATTCCTCTCGTTTTATTATCGTCAGG

AGAGCAAAGAGTAATTGTTGTAATACCTAGTTCAT

TGCATGATTTACCACTCAAAAAGTCTAGCAAGTTG

ATTTCTTTTTTACCTTCAAGCCACTCAAGCCTTAT

GGAAGGAAAAGCAACTCCATCTTCATCTACATGTT

TTTCAAGACATAAAAATTTTAGTTTTAAACCGCTA

TCTTTTATTTTTCTTAATACTTCTTTTTTCGTTTC

ATCTGTAACAAATCCTGTAATTATAGGTCGTTCAC

GATAATTCATATCATACAATTTGCCATTGCCCAGC

ATATCAGCATGAAAATAATCAGAAGAAAATTTCTC

CCACGAATCCTTATCTGAAAAGTGATGGCCATGTG

TATTACCAGGAATAAAATCACTTACAGAATTTCTA

CTAAAACCCTTATCAAGAAAAAGTGGAACTAAAGT

TTCCCCAAACTTCTTTTTACTTGACCAAATCGATT

TTCTTAAAGCATTTAACATACTAACCCCCATATTA

ATGCCATAATAAATTTATTATGACATTACGGAATA

TGCTAAGTCAAGTTTATAACTTTAAATTTTTATGA

AAATTAACAAAAAAATCATACTTTACATGGCATGA

AAAACGCCGTATTATACCACCTCTAGTAGAAATCA

AGCTTAAAATTTAAGGGAATTTGCGTAAAGGGCAT

TTCTGCCCTTTACACGCATTTAAATTTTTAGTAGA

TTCGAGCTGCAAACAAAAAATCTTACTAAGACACA

TGAGGCACAAAAACAACAGAACGTATCGCACCAGA

ACGTATCAAAAAAAATTGTACAGAAACGAAAAAAA

GAGTCAAGCAAAAAAAAGCTTGACTTCCCATTATC

GCGTCTATCACAACTTCAGCATAAGAGGAAGCCTT

CATATAGTTAACGTAAACGGTAAATATGTGCAGGC

GCAAATAGGCTCTAGAAGGCGAATAAAGGCGCGAG

AAAAGTCAATTGAGCTTAAGCGTCCGATAAGAACT

TTCGACACGCGTCTTACTGGCAGTGAACTACTACA

-continued

AGTTTTAAAAAACAAGGAAGTAAGATGGTTTAAAA

ACGGCACTGCTGTTCCTCCGGAACATAGTACTTAT

CTTTTAGAGGCTTTTAATCCACACAAAGCAAAGAA

AATCTTTTCCAGTTCAGCGCAAAAAGCGGCGGAAA

AATACTTTGTCAGAGTAGTAAAAGAAAAATTTCGC

GATTTAAAAACAGCGAAAGCACCGGATGTGCTCGC

AATTAGAGAGAAAGCAGTAGAAAAAGTTCTCGAAA

AGTTCAAGAATCACTGTGAATTTATATCAATAGAG

GTATACATTAAGAACTTATGGATAACTTTCGACGA

ACATCTCTATAGCAAGATGAGCATGAAAGAAAAAG

TGGACCACCACATCGATTTGATCATACAAAACACT

AGTCAGGAGAGAGAGGAAGAACTGCTTGCTGCAGG

AGAAACGCCGGAGGAAGTATACCACACTTTCAGAA

CGGTCCAGGGATCGAATCTGTATCGCATCAGGCTG

CTGAGCGAGCGAGGAGGAGCTGCGCTTGAGATATA

CATCAGGAAAGAGCTGCAGCGGCGGCTAAAACTCC

TTTTCAACCACTTTAAAGATAGAATGATCAGAATT

GGTGTCGACACGGAGAAAGACTTTTTCTCGATTGC

CCGCCGGCATTTTTCGTTTTTATTCACGAAGAAAT

ACGTCAAAAACAGAAAGAAAGTGATGAGGGAGGTA

CGTCATATCCTTGCTCTCATCAGAGAAAACCCGTT

TGATGTTCTGAAGGATTACGACAATTTATGCAAAT

TTGATCCACCACCTCTCTAGAGAAAGCAAAAATGT

TACCCGAAAGTGACCCCCATCATGCTTAATTGAAA

AAAACAATAAAAAGTGCGACGATTATATTAGTTTT

AGTATTAGGAAATTGCTCTTACTTAAAAAATAATA

AGGTAAAATCCTTTCATTTTTCTTTCTATTTAAAA

AAGTTATACACAATACAATATATAAAAGTATATAT

TATAGTTTTTATAGTATATTCTTATTATAAAAGTC

GAAAGTACCCCTATATTATCACTATAAAGGAAGAA

AGAGTTATAGAGAGGTTATTCACAGTTATTTCTTC

AAAGTTTTAATGTATTCAGTTAAAGCCCTGAATCC

AATGTTAGAGACCGTATCTTGAGTTTTAAAGGCTA

TTTCTTTCACTTCTCTACAAAGATCAGGTGAAAGC

CTTAATGTTAATCGTTGTTTTTGTTCCCGTTCTTT

AATAAAAGCATGTCTCTGTTGATCCTCTTTTTTAT

AACCCACATCAGAGATTCTATGTAATCTATGTTCC

TTCGATCTATGTTCTGAAATTACAGGCATTATTAT

TTTCTTAGTGTCCACTAAAAACCTCCTTGTAAATA

GATTTAATTTCCTCAATTGCCTTTGAATCGGCTGA

-continued

TTCAACAATCGTCAAACCTTCAAGAGAGGAGTCTT

CAACTACAGCCCGCTGACTCAAAAAACTATCGAGC

CTTGTTAAATTATCAAAATGACTTAGAAAACTATC

ACATTTTGTGATTATTTTTTTAGCTCTAGTTGGAT

TAGTATTAACTCGATTAAGTAGGATTCTTGCTTTA

AAGATTTTATTACAACTCCGAGCACCGGCAATTAA

ATTGTTAAGAACTTTGAATGTCCACACATCAATTC

CAGATGGAACAATCGGAAAGATCACTATATCAGCT

AGTAATAAAGCAGCTCTTAATGCTTCATTATTACC

ACCACCTACATCAACAACAATGTCTTGATATTCAG

AATGCAAAGCTGTTAGTTCATTTTTGATTGCTATG

CCATCTCGTGGCCCTTGACTACTGCTAATCACCGG

TAAGTTTATGTCCTGATCTCGTTGAGATGCCCACA

AGCTGGCCATCTCTTGATGATCAATATCATAGAGG

TGAACGTTTCTACCTTCTAGAGTACGCATTAATGC

TATGTTTGTGGCTATGGTTGTTTTACCACAACCAC

CTTTCTGACCACCGACTAATATTATCATGCCTACC

TTAGTTATAAAACAACATCTTAGTGACACGTCACC

ATGTCGTCAAGTCAACGTGTCACTATGTCAACGTG

TCACCATGTCAACGTGTCAACGTGTCACCATGTCA

CCATGTCACCATGTCGCAAACAAGGCTTATTCACT

GAATAATCAACAATTCTGTTAATAACTACAAACAC

TCAAGCAAGAAAAAGGAGCTTTTGCTCGCACAGAA

ACATCGTTTTTAGCGTCGTTCTTCAAAATCGTATA

ATTATACACGTTATCGGGGCAAGGTATCCCTAGAC

GGTTTCTTTCAGGAAACCACATGATGAACTCACTG

AGGACATCGGCGATATCATCGGTGAACTCAGTTTC

AGTATGAATCTTTTCAAACTCATCAAATATCAAAT

AATGAAAATCTCTTTCCGCTTTCTCAAGAAAGATA

TGACCTTGCTCAACAAACTGACTGCAAGACTGAAA

CACTTCCATCTTTGACCTCGTTCTTCTTGAGCCTA

AAATCAGTGTGTCTGGCAATAGCATTCGAAGATCT

GCGATCACCTTAAAGCCAATACCGTGTTCTTCCAC

GACTACTGCGTGCAGCCTATGCTCATATTTACTGA

GAAACTCATGAATATCGTGTTCAACTGAACTCGGG

TCAAGCTTTCTTGCCAATAAATCCACCCATACTCC

ACATCTTTTTGGCTGATGGGCAAAATCACTCTTCG

TAAAGAACGGCTGAAACACTCCTACCGCTGTTCTA

TCAAGTGTTTTCAGCGAACCACTGTTGAGATCGAT

AAATGCTACCAGATCTTTTTCTCCTATTTTCTCAT

AAGGAAAATCAATATTCCTAATAATGTCTTGCAAT

-continued

ACTATACTTAGTATTAACTTCTGTGTCATTTCTCC
CGAGCATCAGCAAAAGCCAATGACTCTGTATACTC
AACCTACCATAATCTGTCAACATAATTCTTTATTG
AAAATTTATTAACACAGGTTGAGTATTTTTCAATT
ATATCTATAATAAAAAGATGGATATGAAATACCGT
TATTGGGACTCTCCAGAAACAGAAGAGATTGTTCG
CAAAACTTACGATGCTCAATTAAAGATTATAGATG
ATATAAAAAATGATAAAGAACTTGGGAAATTAGCA
TTAGAAATATTATATACCGTTACTTACTGTAATTT
ACGGGATCTTCCCTTATTAACTTTTTATAGTTCAG
CTACCACACATCATAATAATCTTTATGGTGGTGTG
GATCTTCATACACTTTATGAACTTTATGATGAACC
TTTTGAAGATGCTGAAGATTTACTAATGGCTTCTT
TTGATTTATTAGTAAAATATCAATTGGTTGATTGT
TATAAAAAATGGAGTGATACAAGTGTTATCCATGCA
TCAAGTCACTCGAAGCAATATACAGCTTATGTTAA
AAGAACAAGGTATAGAAGAAGAAGTTTTAAAAAAA
GCCATAAGTGTATTATCGAGATTTCTGAGTGAGCT
CAAATATTCATTAGATGACAAGGATGAAGGAGCGG
GTTTTTTTTCTTTCATAGAAGGAATAATTCCGTAT
GCGTGCTCTAATGCACAACACGTTTTATATCATGC
AGAGGAATACAAAGAATTAAATAAGTATTGCGAAA
AAGAAAAAATTAGAACTTTTAATTGATTATTTCGTA
GCAGCAAGACTTTATCAAAAACATAGTATTACTAT
ACATCACTAAATATTAAATATATTTTATACAGCCC
TCCTTCCTCTTCACCTTAACAATTCTTTATTGAAA
ATTTCATGAAAATGTTGTATAATTGTAGAGTAGTA
GAACTCGGTAAAACTCATGGCAAACGCTAATTTAG
CTTTCAGTAAAGAAACTTTACAGCATCTTGCTGAA
TTATCTGAACTTACTAAGCAACCTGCTCAAGCATT
AGCAGAAAAACTACTTAAAGAAGCAATCGAGCTTG
AAATCGAAGATTTTTTAGTTTCTAAAATTTCTGAT
GAGCGTGATGTCGAAGGTGCAGAAATGATTAAAAG
TGAGGATGTAGATTGGGATACACTATTATCTTCGT
AGGAAAGGTTATTAGAAAAGACCTTCCTGACCTTC
CAAAAACAATAAGATTGAGGGTCGTAAATGCGATA
AATGAAAGACTTACAGTTGATCCAATGAACCTCGG
TGAACCATTGCACCACAGCTTAAAAGGACGTAGAA
GGTTAAGAGTTGGTGAGTACCGTGTGATTTACAGA
GTAAATCAATTAGAACAAATAGTGACCATCACAGA

-continued

GATAGGACATAGATGTGATATTTATAAAAAAATAAA
TATAAACATTAAATATACATTATACAGCCCTTCTT
CCTGATCCATTCTTCACCTTAGGCGGCTTTGCTCA
GCTCAAAAATAACTATTTTTTTGGGTACCCCCCAC
TATAAGTTATATTATATTATATTATTTATATATAA
TATAATATAACTCATTGGGAGAGGCGACGAAAACA
AGATCTTGAGTTTGAGGAGCCTCCGGTTTTAGGTG
AAGAATGGATCAGGAAGAAGGGCTCAGGGTCGATG
AGGACGTAAGGCCAATATTTGATTATCTCAAAGAC
TACAGAGACTACATCGATAAACGGCTAGCAAATCC
CGACGAAATAGAAGGAATAACCACAGGAATAAAGG
AGCTTGACACAATAACAGGTGGCTTCAAGGAAGGA
GAGCTCTCTGTGCTTGCAGCACGCACCTCAATTGG
CAAGACTTCAATAGCACTACACATGGCTCTAGAGG
CCGCAAAGCTCTTAAATGACCACGAGTATGTCTGC
TTCTTCTCCCTTGAAATGTCAGCCAATCAACTCAT
CAACAGAATAATCAGCATCAAAGTCAATGAGACAG
TCAACACTATCATTAAAAACAAG parA-like (GP-10):

SEQ ID NO: 4

ATGATAATATTAGTCGGTGGTCAGAAAGGTGGTTG
TGGTAAAACAACCATAGCCACAAACATAGCATTAA
TGCGTACTCTAGAAGGTAGAAACGTTCACCTCTAT
GATATTGATCATCAAGAGATGGCCAGCTTGTGGGC
ATCTCAACGAGATCAGGACATAAACTTACCGGTGA
TTAGCAGTAGTCAAGGGCCACGAGATGGCATAGCA
ATCAAAAATGAACTAACAGCTTTGCATTCTGAATA
TCAAGACATTGTTGTTGATGTAGGTGGTGGTAATA
ATGAAGCATTAAGAGCTGCTTTATTACTAGCTGAT
ATAGTGATCTTTCCGATTGTTCCATCTGGAATTGA
TGTGTGGACATTCAAAGTTCTTAACAATTTAATTG
CCGGTGCTCGGAGTTGTAATAAAATCTTTAAAGCA
AGAATCCTACTTAATCGAGTTAATACTAATCCAAC
TAGAGCTAAAAAAATAATCACAAAATGTGATAGTT
TTCTAAGTCATTTTGATAATTTAACAAGGCTCGAT
AGTTTTTTGAGTCAGCGGGCTGTAGTTGAAGACTC
CTCTCTTGAAGGTTTGACGATTGTTGAATCAGCCG
ATTCAAAGGCAATTGAGGAAATTAAATCTATTTAC
AAGGAGGTTTTTAGTGGACACTAA

RelBE operon, GP-03/04:

SEQ ID NO: 5

TTGGTAAAACTTATGGCAGATTCAAGGATTAATGT
AACCTTCGATACAGAAACTTCACAGCACCTTATTG

-continued

AACTAGCTAAAGCTACCAAGCAGTCTGTTCAAAAA

TTAGCAGGAAAGTTAGTCAAAGAAGCAATTGAGCT

TGAAGCAGAAGACATTGCGTTTTCTAAAATTATTA

GAGAATTAAGTGATGATGATGCGGAAGAAATAGAA

GATAGTGAAGACATCTGGAAATAAACGTTATACTA

TCAAATATCTCAAACATGTTATTAAGAGGAATATA

CCTTCCTTACCAGAAGACATTAAACCAAGTATTAA

AGAAGCAATAAAAGAATATCTTGAGACTGATCCTA

TTGCTAGCGGTGTATCATTACGCAATAGATTAAAG

GGATATCGCAGAATACGAGTGGGTGATTATCGTAT

CGTCTACCGTGTAGATACTGCAAAACGTATAGTAA

CTGTTGTCTCAATAGGACATAGAGATAACATTTAC

AATCAGGCAATATTAGACTTACTAAAACGTTAA

RelBE operon, GP-13/14:

SEQ ID NO: 6

ATGGCAAACGCTAATTTAGCTTTCAGTAAAGAAAC

TTTACAGCATCTTGCTGAATTATCTGAACTTACTA

AGCAACCTGCTCAAGCATTAGCAGAAAAACTACTT

AAAGAAGCAATCGAGCTTGAAATCGAAGATTTTTT

AGTTTCTAAAATTTCTGATGAGCGTGATGTCGAAG

GTGCAGAAATGATTAAAAGTGAGGATGTAGATTGG

GATACACTATTATCTTCGTAGGAAAGGTTATTAGA

AAAGACCTTCCTGACCTTCCAAAAACAATAAGATT

GAGGGTCGTAAATGCGATAAATGAAAGACTTACAG

TTGATCCAATGAACCTCGGTGAACCATTGCACCAC

AGCTTAAAAGGACGTAGAAGGTTAAGAGTTGGTGA

GTACCGTGTGATTTACAGAGTAAATCAATTAGAAC

AAATAGTGACCATCACAGAGATAGGACATAGATGT

GATATTTATAAAAAATAA

Primer 263F:

SEQ ID NO: 7

CTAGAGGCCGCAAAGCTCTT

Primer 2127R:

SEQ ID NO: 8

CGTCTTGTTCGATGCTCCCT

-continued

Primer EC_4F:

SEQ ID NO: 9

ACACATCGAGCTAATACCCGT

Primer EC_4R:

SEQ ID NO: 10

CCAAGCTCTGGCATTAAACAGA

Primer LC01490:

SEQ ID NO: 11

GGTCAACAAATCATAAAGATATTGG

Primer HCO2198:

SEQ ID NO: 12

TAAACTTCAGGGTGACCAAAAAATCA

Prime Wspec-F:

SEQ ID NO: 13

CATACCTATTCGAAGGGATAG

Primer Wspec-R:

SEQ ID NO: 14

AGCTTCGAGTGAAACCAATTC

SEQ ID NO: 15

CGTCTTGTTCGATGCTCCCT

SEQ ID NO: 16

CTAGAGGCCGCAAAGCTCTT

SEQ ID NO: 17

GCCTACCTTAGTTATAAAACAACATCTTAGTGA

CAC

SEQ ID NO: 18

CAAGGCTTATTCACTGAATAATCAACAATTCTG

SEQ ID NO: 19

AGCCCTTCTTCCTGATCCATTCTTCACCTTAGGCG

GCTTTGCTCAGCTCAAAAATAACTATTTTTTTGGG

TACCCCCCACTATAAGTTATATTATATTATATTAT

TTATATATAATATAATATAACTCATTGGGAGAGGC

GACGAAAACAAGATCTTGAGTTTGAGGAGCCTCCG

GTTTTAGGTGAAGAATGGATCAGGAAGAAGGGCT

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A non-naturally occurring plasmid comprising a first nucleic acid sequence capable of transforming a *Wolbachia* cell, wherein the first nucleic acid sequence comprises a transposase encoded by a nucleotide sequence at least 90% identical to SEQ ID NO: 1.

2. A non-naturally occurring plasmid comprising a first nucleic acid sequence capable of transforming a *Wolbachia* cell, wherein the first nucleic acid sequence comprises a plasmid partition protein A (ParA)-like gene at least 90% identical to SEQ ID NO:4.

3. A non-naturally occurring plasmid comprising a first nucleic acid sequence capable of transforming a *Wolbachia* cell, wherein the first nucleic acid sequence comprises a RelBE toxin-antitoxin operon at least 90% identical to SEQ ID NO:5 or SEQ ID NO:6.

4. The plasmid of claim 1, wherein the transposase is encoded by SEQ ID NO: 1.

5. The plasmid of claim 1, further comprising a second nucleic acid sequence, wherein the second nucleic acid sequence is a heterologous nucleic acid sequence.

6. The plasmid of claim 1, wherein the plasmid further comprises a selectable marker comprising a tetracycline resistance marker or a green fluorescent protein (GFP) marker.

7. The plasmid of claim 5, wherein the heterologous nucleic acid sequence comprises a heterologous gene.

8. The plasmid of claim 7, wherein the heterologous gene is operably linked to a *Wolbachia* surface protein (wsp) promoter active in the *Wolbachia* cell.

9. The plasmid of claim 2, wherein the ParA-like gene comprises SEQ ID NO: 4.

10. The plasmid of claim 2, further comprising a second nucleic acid sequence, wherein the second nucleic acid sequence is a heterologous nucleic acid sequence.

11. The plasmid of claim 2, wherein the plasmid further comprises a selectable marker comprising a tetracycline resistance marker or a green fluorescent protein (GFP) marker.

12. The plasmid of claim 10, wherein the heterologous nucleic acid sequence comprises a heterologous gene.

13. The plasmid of claim 12, wherein the heterologous gene is operably linked to a *Wolbachia* surface protein (wsp) promoter active in the *Wolbachia* cell.

14. The plasmid of claim 3, wherein the RelBE toxin-antitoxin operon comprises SEQ ID NO: 5 or SEQ ID NO: 6.

15. The plasmid of claim 3, further comprising a second nucleic acid sequence, wherein the second nucleic acid sequence is a heterologous nucleic acid sequence.

16. The plasmid of claim 3, wherein the plasmid further comprises a selectable marker comprising a tetracycline resistance marker or a green fluorescent protein (GFP) marker.

17. The plasmid of claim 15, wherein the heterologous nucleic acid sequence comprises a heterologous gene.

18. The plasmid of claim 17, wherein the heterologous gene is operably linked to a *Wolbachia* surface protein (wsp) promoter active in the *Wolbachia* cell.

* * * * *